US009782452B2

(12) United States Patent
Scandura et al.

(10) Patent No.: US 9,782,452 B2
(45) Date of Patent: Oct. 10, 2017

(54) METHODS FOR STIMULATING HEMATOPOIETIC RECOVERY BY INHIBITING TGFβ SIGNALING

(71) Applicants: Joseph Scandura, New York, NY (US); Fabienne Brenet, New York, NY (US)

(72) Inventors: Joseph Scandura, New York, NY (US); Fabienne Brenet, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/359,756

(22) PCT Filed: Nov. 21, 2012

(86) PCT No.: PCT/US2012/066225
§ 371 (c)(1),
(2) Date: May 21, 2014

(87) PCT Pub. No.: WO2013/078286
PCT Pub. Date: May 30, 2013

(65) Prior Publication Data
US 2014/0328860 A1 Nov. 6, 2014

Related U.S. Application Data

(60) Provisional application No. 61/562,766, filed on Nov. 22, 2011, provisional application No. 61/579,447, filed on Dec. 22, 2011, provisional application No. 61/710,311, filed on Oct. 5, 2012.

(51) Int. Cl.
| | |
|---|---|
| *A61K 39/395* | (2006.01) |
| *A61K 31/498* | (2006.01) |
| *A61K 31/7052* | (2006.01) |
| *C07K 16/22* | (2006.01) |
| *C07K 16/28* | (2006.01) |
| *C12N 15/113* | (2010.01) |
| *A61K 38/17* | (2006.01) |
| *C07K 14/495* | (2006.01) |
| *A61K 45/06* | (2006.01) |
| *A61K 31/713* | (2006.01) |

(52) U.S. Cl.
CPC ........ *A61K 38/179* (2013.01); *A61K 31/498* (2013.01); *A61K 31/7052* (2013.01); *A61K 31/713* (2013.01); *A61K 45/06* (2013.01); *C07K 14/495* (2013.01); *C07K 16/2863* (2013.01); *C12N 15/1136* (2013.01)

(58) Field of Classification Search
None
See application file for complete search history.

(56) References Cited

U.S. PATENT DOCUMENTS

| | | | |
|---|---|---|---|
| 5,278,145 A | 1/1994 | Keller et al. | |
| 5,939,391 A * | 8/1999 | Tsyrlova | A61K 38/42 514/13.5 |
| 6,114,598 A | 9/2000 | Kucherlapati et al. | |
| 6,150,584 A | 11/2000 | Kucherlapati et al. | |
| 6,162,963 A | 12/2000 | Kucherlapati et al. | |
| 6,184,226 B1 | 2/2001 | Chakravarty et al. | |
| 6,476,031 B1 | 11/2002 | Chakravarty et al. | |
| 7,053,095 B2 | 5/2006 | Munchhof et al. | |
| 7,087,626 B2 | 8/2006 | Beight et al. | |
| 7,265,225 B2 | 9/2007 | Beight et al. | |
| 7,407,958 B2 | 8/2008 | Kim et al. | |
| 7,723,486 B2 | 5/2010 | Ledbetter et al. | |
| 2001/0018054 A1 * | 8/2001 | Hanna | A61K 39/00 424/184.1 |
| 2005/0232896 A1 * | 10/2005 | Schwarz | C07K 14/70578 424/85.1 |
| 2007/0135354 A1 | 6/2007 | Wallner et al. | |
| 2009/0285810 A1 * | 11/2009 | Adams | C07K 16/22 424/133.1 |
| 2010/0183543 A1 | 7/2010 | Yonehiro et al. | |
| 2015/0086547 A1 * | 3/2015 | Harper | A61K 31/425 424/133.1 |

FOREIGN PATENT DOCUMENTS

| | | |
|---|---|---|
| EP | 0945464 A1 | 9/1999 |
| RU | 2414926 C1 | 3/2011 |
| WO | 01/11011 A2 | 2/2001 |

OTHER PUBLICATIONS

Farese et al. Acceleration of hematopoietic reconstitution with a synthetic cytokine (SC-55494) after radiation-induced bone marrow aplasia. Blood. Jan. 15, 1996;87(2):581-91.*
Zhou et al., "Inhibition of the TGF-β receptor I kinace promoted hematopoiesis in MDS" Blood (Oct. 15, 2008) pp. 3434-3443, vol. 112, No. 8.
Selikhova, Y.U., "Kharakteristika immunnoy I krovetvornoy sustemy u bolnykh rakom molochnoy zhelezy na razlichnykh etapakh protivoopukholevoy terapii" *Avtoreferat dissertatsii* (2008) pp. 1-17, URL: http://www.dissercat.com/content/kharakteristika-immunoi-i-krovetvornoi-sustemy-u-bolnykh-rakom-molochnoi-zhelezy-na-razlich.
Grivtsova, L.U. et al., "Subpopulyatsii transplantiruemykh stvolovykh krovetvornykh kletok" *Consilium Medicum* (2006), pp. 1-9, vol. 8, No. 1, URL: http://www.consilium-medicum.com/article/8641.
Levine, A.M., "Anemia, Neutropenia and Thrombocytopenia: Pathogenesis and Evolving Treatment Options in HIV-Infected Patients CME" (Jun. 5, 2002) pp. 31, URL: http://www.avpivnik/ru/works/translations/Anemia_Neutropenia_and_Thrombocytopenia.doc.
International Search Report dated Apr. 4, 2013 issued in International Application No. PCT/US2012/066225.

(Continued)

*Primary Examiner* — David Romeo
(74) *Attorney, Agent, or Firm* — Scully Scott Murphy & Presser

(57) ABSTRACT

This disclosure demonstrates that blockade of TGFβ signaling after a hematopoietic stress (e.g., chemotherapy, transplantation, and infection) accelerates hematopoietic reconstitution and delays the return of cycling hematopoietic stem and progenitor cells (HSPCs) to quiescence. TGFβ blockade in these settings promotes multilineage hematopoietic regeneration by prolonging HSPC cycling and by promoting HSC self-renewal, and is useful for treating hematologic deficiencies caused various hematopoietic stresses.

12 Claims, 14 Drawing Sheets

(56) References Cited

OTHER PUBLICATIONS

Akhurst, R.J. et al., "Targeting the TGFBeta signaling pathway in disease" Nature Reviews (Oct. 2012) pp. 790-812, vol. 11.

Arteaga, C.L. et al., "Anti-Transforming Growth Factor (TGF)-Beta Antibodies Inhibit Breast Cancer Cell Tumorigenicity and Increase Mouse Spleen Natural Killer Cell Activity: Implications for a Possible Role of Tumor CEll/Host TGF-Beta Interations in Human Breast Cancer Progression" Journal Clin. Invest. (Dec. 1993) pp. 2569-2576, vol. 92.

Bandyopadhyay, A. et al., "A Soluble Transforming Growth Factor Beta Type III receptor Suppresses Tumorigenicity and Metastasis of Human Breast Cancer MDA-MD-231 Cells" Cancer Research (1999) pp. 5041-5046, vol. 59.

Batard, P. et al., "TGF-Beta1 maintains hematopoietic immaturity by a reversible negative control of cell cycle and induces CD34 antigen up-modulation" Journal of Cell Science (2000) pp. 383-390, vol. 113.

Bitko, V. et al., "Phenotypic silencing of cytoplasmic genes using sequence-specific double-stranded short interfering RNA and its application in the reverse genetics of wild type negative-strand RNA viruses" BMC Microbiology (2001) pp. 1-11, vol. 1.

Benigni, A. et al., "Add-On Anti-TGF-Beta Antibody to ACE Inhibitor Arrests Progressive Diabetic Nephropathy in the Rat" J. Am. Soc. Nephrol (2003) pp. 1816-1824, vol. 14, No. 7.

Blank, U. et al., "The role of Smad signaling in hematopoiesis and translational hematology" Leukemia (2011) pp. 1379-1388, vol. 25.

Blank, U. et al., "Smad7 promotes self-renewal of hematopoietic stem cells" Blood (2006) pp. 4246-4254, vol. 108.

Burton, D.R. et al., "Human Antibodies from Combinatorial Libraries" Advances in Immunology (1994) pp. 191-280, vol. 57.

Cheng, T. et al., "Stem cell repopulation efficiency but not pool size is governed by p27kip" Nature Medicine (Nov. 2000) pp. 1235-1240, vol. 6, No. 11.

Cech, T., "Robozymes and Their Medical Implications" JAMA (Nov. 1988) pp. 3030-3034, vol. 260, No. 20.

Carter, P. et al., "Humanization of an anti-p185HER2 antibody for human cancer therapy" Proc. Natl. Acad. Sci. USA (May 1992) pp. 4285-4289, vol. 89.

Cheng, T. et al., "Hematopoietic Stem Cell Quiescence Maintained by p21cip1/waf1" Science (2000) pp. 1804-1808, vol. 287.

Brenet, F. et al., "TGFb pathway activation limits hematopoietic recovery from chemotherapy" Poster Presentation (2011) Abstract 1113.

Capron, C. et al., "A major role of TGF-b1 in the homing capacities of murine hematopoietic stem cell/progenitors" Blood (2010) pp. 1244-1253, vol. 116.

Cheng, T. et al., "Transforming growth factor b1 mediates cell-cycle arrest of primitive hematopoietic cells independent of p21 Cip1/Waf1 or p27Kip1" Blood (2001) pp. 3643-3649, vol. 98.

Cui, Q. et al., "Selective inhibition of TGF-beta responsive genes by Smad-interacting peptide aptamers from FoxH1, Lef1 and CBP" Oncogene (2005) pp. 3864-3874, vol. 24.

Dickson, M.C. et al., "Defective haematopoiesis and vasculogenesis in transforming growth factor-Beta1 knock out mice" Development (1995) pp. 1845-1854, vol. 121.

Ehata, S. et al., "Ki26894, a novel transforming growth factor-Beta type I receptor kinase inhibitor, inhibits in vitro invasion and in vivo bone metastasis of a human breast cancer cell line" Cancer Sci. (Jan. 2007) pp. 127-133, vol. 98, No. 1.

Fortunel, N. et al., "Specific dose-response effects of TGF-beta1 on developmentally distinct hematopoietic stem/progenitor cells from human umbilical cord blood" The Hematology Journal (2000) pp. 126-135, vol. 1.

Fortunel, N. et al., "Transforming growth factor-beta: pleiotropic role in the regulation of hematopoiesis" Blood (2000) pp. 2022-2036, vol. 96.

Elbashir, S.M. et al., "Duplexes of 21-nucleotide RNAs mediate RNA interference in cultured mammalian cells" Nature (May 2001) pp. 494-498, vol. 411.

Griffiths, A.D. et al., "Building an in vitro immune system: human antibodies from phage display libraries" Protein Engineering of Antibody Molecules for Prophylactic and Therapeutic Applications in Man (1993) Nottingham Academic, pp. 45-64.

Gorelik, L. et al., "Abrogation of TGFb Signaling in T Cells Leads to Spontaneous T Cell Differentiation and Autoimmune Disease" Immunity (Feb. 2000) pp. 171-181, vol. 12.

Dumont, N. et al., "Targeting the TGFBeta signaling network in human neoplasia" Cancer Cell (Jun. 2003) pp. 531-536, vol. 3.

Grzegorzewski, K. et al., "Recombinant transforming growth factor Beta1 and Beta2 protect Mice from acutely lethal doses of 5-fluorouracil and doxorubicin" The Journal of Experimental Medicine (Sep. 1994) pp. 1047-1057, vol. 180.

Jakobovits, A., "The long-awaited magic bullets: therapeutic human monoclonal antibodies from transgenic mice" Exp. Opin. Invest. Drugs (1998) pp. 607-614, vol. 7, No. 4.

Jeffries, A.C. et al., "A catalytic 13-mer ribozyme" Nucleic Acids Research (1989) pp. 1371-1377, vol. 17, No. 4.

Jones, P.T. et al., "Replacing the complementarity-determining regions in a human antibody with those from a mouse" Nature (May 1986) pp. 522-525, vol. 321, No. 29.

Karlsson, G. et al., "Smad4 is critical for self-renewal of hematopoietic stem cells" J. Exp. Med (Mar. 2007) pp. 467-474, vol. 204, No. 3.

Kiel, M.J. et al., "SLAM Family Receptors Distinguish Hematopoietic Stem and Progenitor Cells and Reveal Endothelial Niches for Stem Cells" Cell (Jul. 2005) pp. 1109-1121, vol. 121.

Hjelmeland, M.D. et al., "SB-431542, a small molecule transforming growth factor-beta-receptor antagonist, inhibits human glioma cell line proliferation and motility" Mol. Cancer Ther. (2004) pp. 737-745, vol. 3.

Haseloff, J. et al., "Simple RNA enzymes with new and highly specific endoribonuclease activities" Nature (Aug. 1988) pp. 585-591, vol. 334.

Kim. S. et al., "Three-dimensional model of the active site of the self-splicing rRNA precursor of Tetrahymena (intervening sequence/intron/RNA splicing/RNA structure/"ribozyme")" Proc. Natl. Acad. Sci. USA (Dec. 1987) pp. 8788-8792, vol. 84.

Koehler, G. et al., "Derivation of specific antibody-producing tissue culture and tumor lines by cell fusion" Eur. J. Immunol. (1976) pp. 511-519, vol. 6.

Korpal, M. et al., "Targeting the transforming growth factor-b signalling pathway in metastatic cancer" European Journal of Cancer (2010) pp. 1232-1240, vol. 46.

Larsson, J. et al., "Abnormal angiogensis but intact hematopoietic potential in TGF-Beta type 1 receptor-deficient mice" The EMBO Journal (2001) pp. 1663-1673, vol. 20, No. 7.

Larsson, J. et al., "TGF-b signaling-deficient hematopoietic stem cells have normal self-renewal and regeneratice ability in vivo despite increased proliferative capacity in vitro" Blood (2003) pp. 3129-3135, vol. 102.

Leveen, P. et al., "Induced disruption of the transforming growth factor beta type II receptor gene in mice causes a lethal inflammatory disorder that is transplantable" Blood (2002) pp. 560-568, vol. 100.

Larsson, J. et al., "Quiescence of hematopoietic stem cells and maintenance of the stem cell pool is not dependent on TGF-Beta signaling in vivo" Experimental Hematology (2005) pp. 592-596, vol. 33.

Miyamoto, K. et al., "Foxo3a Is Essential for Maintenance of the Hematopoietic Stem Cell Pool" Cell Stem Cell (Jul. 2007) pp. 101-112, vol. 1.

Muraoka, R.S. et al., "Blockade of TGF-Beta inhibits mammary tumor cell viability, migration, and metastases" The Journal of Clinical Investigation (Jun. 2002) pp. 1551-1559, vol. 109, No. 12.

Mead, A.L. et al., "Evaluation of Anti-TGF-Beta2 Antibody as a New Postoperative Anti-scarring Agent in Glaucoma Surgery" Investigative Ophthalmology & Visual Science (Aug. 2003) pp. 3394-3401, vol. 44, No. 8.

Matsumoto, A. et al., "p57 Is Required for Quiescence and Maintenance of Adult Hematopoietic Stem Cells" Cell Stem Cell (2011) pp. 262-271, vol. 9.

(56) References Cited

OTHER PUBLICATIONS

McCulloch, E.A., "CFU-S: An Assay for Pluriopotent Myelopoietic Stem Cells" Methods in Molecular Medicine: Hematopoietic Stem Cell Protocols (2002) pp. 153-160, vol. 63.

Morrison, S.J. et al., "Cyclophosphamideygranulocyte colony-stimulating factor induces hematopoietic stem cells to proliferate prior to mobilization" Proc. natl. Acad. Sci. USA (Mar. 1997) pp. 1908-1913, vol. 94.

Moon, J.A. et al., "IN-1130, a novel transforming growth factor-beta type I receptor kinase (ALK5) inhibitor, suppresses renal fibrosis in obstructive nephropathy" Kidney Int. (2006) pp. 1234-1243, vol. 70, No. 7.

Muraoka-Cook, R.S. et al., "Dual role of transforming growth factor Beta in manmmary tumorigenesis and metastatic progression" Clinical Cancer Research (Jan. 2005) pp. 937s-943s, vol. 11.

Nagaraj, N.S. et al., "Targeting the transforming growth factor-b signaling pathway in human cancer" Exp. Opin. Investig. Drugs (2010) pp. 77-91, vol. 19, No. 1.

Nam, J.S. et al., "Bone Sialoprotein Mediates the Tumor Cell-Targeted Prometastatic Activity of Transforming Growth Factor b in a Mouse Model of Breast Cancer" Cancer Research (2006) pp. 6327-6335, vol. 66.

Nemunaitis, J. et al., "Phase 1/2 trial of autologous tumor mixed with an allogeneic GVAXs vaccine in advanced-stage non-small-cell lung cancer" Cancer Gene Therapy (2006) pp. 555-562, vol. 13.

Oshima, M. et al., "TGF-b Receptor Type II Deficiency Results in Defects of Yolk Sac Hematopoiesis and Vasculogenesis" Developmental Biology (1996) pp. 297-302, vol. 179, article No. 0259.

Riechmann, L. et al., "Reshaping human antibodies for therapy" Nature (Mar. 1988) pp. 323-327, vol. 332.

Qian, H. et al., "Critical Role of Thrombopoietin in Maintaining Adult Quiescent Hematopoietic Stem Cells" Cell Stem Cell (Dec. 2007) pp. 671-684, vol. 1.

Pfeilschifter, J. et al., "Concentration of Transforming Growth Factor Beta in Human Bone Tissue: Relationship to Age, Menopause, Bone Turnover, and Bone Volume" Journal of Bone and Mineral Research (1998) pp. 716-730, vol. 13, No. 4.

Passegue, E. et al., "Global analysis of proliferation and cell cycle gene expression in the regulation of hematopoietic stem and progenitor cell fates" JEM (Dec. 2005) pp. 1599-1611, vol. 202, No. 11.

Saunier, E. et al., "TGF Beta Inhibition for Cancer Therapy" Current Cancer Drug Targets (2006) pp. 565-578, vol. 6.

Suzuki, E. et al., "A Novel Small-Molecule Inhibitor of Transforming Growth Factor Beta Type 1 Receptor Kinase (SM16) Inhibits Murine Mesothelioma Tumor Growth In vivo and Prevents Tumor Recurrence after surgical resection" Cancer Research (2007) pp. 2351-2359, vol. 67.

Schlingensiepen, K. et al., "Antisense therapeutics for tumor treatment: the TGF-beta2 inhibitor AP 12009 in clinical development against malignant tumors" Recent Results Cancer Res (2008) pp. 137-150, vol. 177.

Scandura, J.M. et al., "Transforming growth factor Beta-induced cell cycle arrest of human hematopoietic cells requires p57KIP2 up-regulation" PNAS (Oct. 2004) pp. 15231-15236, vol. 101, No. 42.

Sitnicka, E. et al., "Transforming growth factor beta 1 directly and reversibly inhibits the initial cell divisions of long-term repopulating hematopoietic stem cells" Blood (1996) pp. 82-88, vol. 88.

Subramanian, G. et al., "Targeting Endogenous Transforming Growth Factor Beta Receptor Signaling in SMAD4-Deficient Human Pancreatic Carcinoma Cells Inhibits Their Invasive Phenotype" Cancer Research (2004) pp. 5200-5211, vol. 64.

Sawyer, T.K., "Novel Oncogenic Protein Kinase Inhibitors for Cancer Therapy" Curr. Med. Chem.—Anti-Cancer Agents (2004) pp. 449-455, vol. 4.

Sawyer, J. et al., "Synthesis and Activity of New Aryl- and Heteroaryl-Substituted Pyrazole Inhibitors of the Transforming Growth Factor-â Type I Receptor Kinase Domain" J. Med.Chemistry (Sep. 2003) pp. 3953-3956, vol. 46, No. 19.

Yamazaki, S. et al., "TGF-b as a candidate bone marrow niche signal to induce hematopoietic stem cell hibernation" Blood (2009) pp. 1250-1256, vol. 113.

Tojo, M. et al., "The ALK-5 inhibitor A-83-01 inhibits Smad signaling and epithelial-to-mesenchymal transition by transforming growth factor-Beta" Cancer Sci (Nov. 2005) pp. 791-800, vol. 96, No. 11.

Yamazaki, S. et al., "Cytokine signals modulated via lipid rafts mimic niche signals and induce hibernation in hematopoietic stem cells" The EMBO Journal (2006) pp. 3515-3523, vol. 25.

Yamazaki, S. et al., "Nonmyelinating Schwann Cells Maintain Hematopoietic Stem Cell Hibernation in the Bone Marrow Niche" Cell (Nov. 2011) pp. 1146-1158, vol. 147.

Uhl, M. et al., "SD-208, a Novel Transforming Growth Factor beta Receptor I Kinase Inhibitor, Inhibits Growth and Invasiveness and Enhances Immunogenicity of Murine and Human Glioma Cells In vitro and In vivo" Cancer Research (2004) pp. 7954-7961, vol. 64.

Verhoeyen, M. et al., "Reshaping human antibodies: Grafting an antilysozyme activity" Science (1988) pp. 1534-1536, vol. 239.

Tran, T. et al., "Inhibiting Tgf-beta signaling restores immune surveillance in the SMA-560 glioma model" Neuro-Oncology (2007) pp. 259-270, vol. 9.

Wilson, A. et al., "Hematopoietic Stem Cells Reversibly Switch from Dormancy to Self-Renewal during Homeostasis and Repair" Cell (Dec. 2008) pp. 1118-1129, vol. 135.

Yang, Y. et al., "Lifetime exposure to a soluble TGF-beta antagonist protects mice against metastasis without adverse side effects" The Journal of Clinical Investigation (Jun. 2002) pp. 1607-1615, vol. 109, No. 12.

Yilmaz, O. et al., "SLAM family markers are conserved among hematopoietic stem cells from old and reconstituted mice and markedlyincrease their purity" Blood (2006) pp. 924-930, vol. 107.

Yingling, J.M. et al., "Development of TGF-Beta Signalling Inhibitors for Cancer Therapy" Nature Reviews Drug Discovery (Dec. 2004) pp. 1011-1022, vol. 3, No. 12.

Yaswen, L. et al., "Autoimmune manifestations in the transforming growth factor-beta 1 knockout mouse" Blood (1996) pp. 1439-1445, vol. 87.

Zou, P., et al., "p57Kip2 and p27Kip1 Cooperate to Maintain Hematopoietic Stem Cell Quiescence through Interactions with Hsc70" Cell Stem Cell (Sep. 2011) pp. 247-261, vol. 9.

Yoshihara, H. et al., "Thrombopoietin/MPL Signaling Regulates Hematopoietic Stem Cell Quiescence and Interaction with the Osteoblastic Niche" Cell Stem Cell (Dec. 2007) pp. 685-697, vol. 1.

Lahn, M. et al., "TGF-Beta inhibitors for the treatment of cancer" Expert Opin. Investig. Drugs (2005) pp. 629-643, vol. 14, No. 6.

Letterio, J. et al., "Autoimmunity Associated with TGF-beta1-Deficiency in Mice Is Dependent on MHC Class II Antigen Expression" J. Clin. Invest. (Nov. 1996) pp. 2109-2119, vol. 98, No. 9.

Sims, M.J. et al., "A humanized CD18 antibody can block function without cell destruction" J Immunol. (Aug. 1993) pp. 2296-2308, vol. 151, No. 4.

Schaefer, B.C. et al., "Observation of Antigen-Dependent CD8+ T-Cell/ Dendritic Cell Interactions in Vivo" Cellular Immunology (Dec. 2001) pp. 110-122, vol. 214, No. 2.

Zhang, P. et al., "Altered cell differentiation and proliferation in mice lacking p57KIP2 indicated a role in Beckwith-Weidemann syndrome" Nature (May 1997) pp. 151-158, vol. 387.

Zamore, P.D., "RNA interference: listening to the sound of silence" Nature Structural Biology (Sep. 2001) pp. 746-750, vol. 8, No. 9.

Yuan, Y. et al., "In vivo self-renewing divisions of haematopoietic stem cells are increased in the absence of the early G1-phase inhibitor, p18INK4C" Nature Cell Biology (May 2004) pp. 436-442, vol. 6, No. 5.

Grzegorzewski, K. et al., "Recombinant Transforming Growth Factor Beta1 and Beta2 Protect Mice from Acutely Lethal Doses of 5-Fluorouracil and Doxorubicin", The Journal of Experimental Medicine, (Sep. 1994), vol. 180, pp. 1047-1057.

Larsson, J. et al., "TGF-Beta signaling-deficient hematopoietic stem cells have normal self-renewal and regenerative ability in vivo despite increased proliferative capacity in vitro", Blood, (Nov. 1, 2003), vol. 102, No. 9, pp. 3129-3135.

(56) References Cited

OTHER PUBLICATIONS

Karlsson, S. et al., "Is TGF-Beta a stemness regulator?", Blood, (Feb. 5, 2009), vol. 113, No. 6, 2 pages.
Blank, U, et al., "TGF-Beta signaling in the control of hematopoietic stem cells", Blood, (Jun. 4, 2015), vol. 125, No. 23, pp. 3542-3550.
Brenet, F. et al., "TGFBeta restores hematopoietic homeostasis after myelosuppressive chemotherapy", JEM, (Feb. 25, 2013), 18 pages.
Kim, J.Y. et al., "Up-regulated macrophage migration inhibitory factor protects apoptosis of dermal fibroblasts in patients with systemic sclerosis", Clinical and Experimental Immunology, (May 2008), vol. 152, pp. 328-335.

* cited by examiner

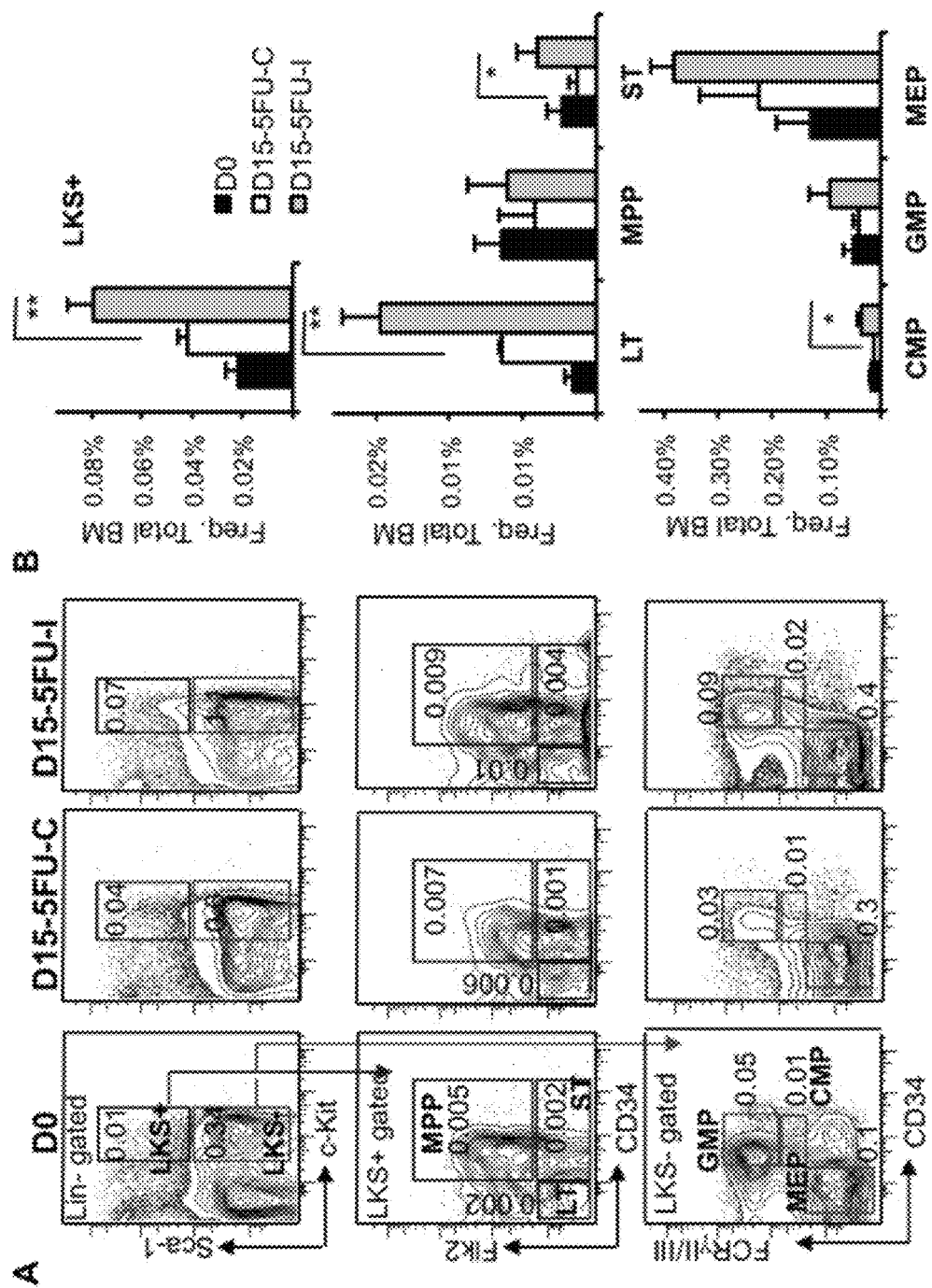
Figures 3A-B

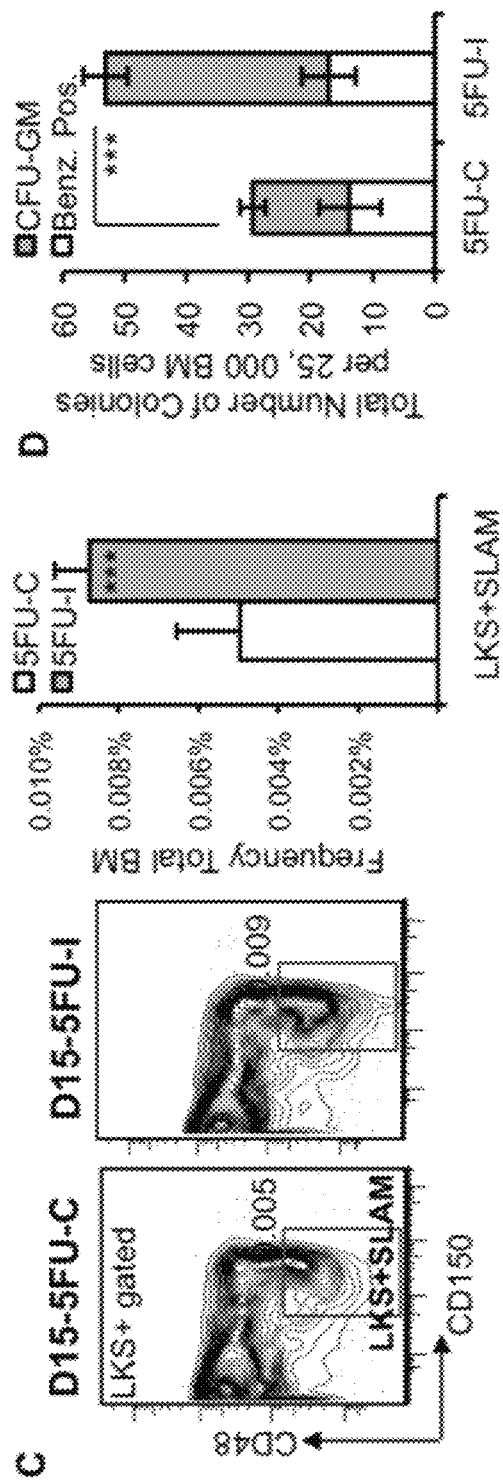
Figures 3C-D

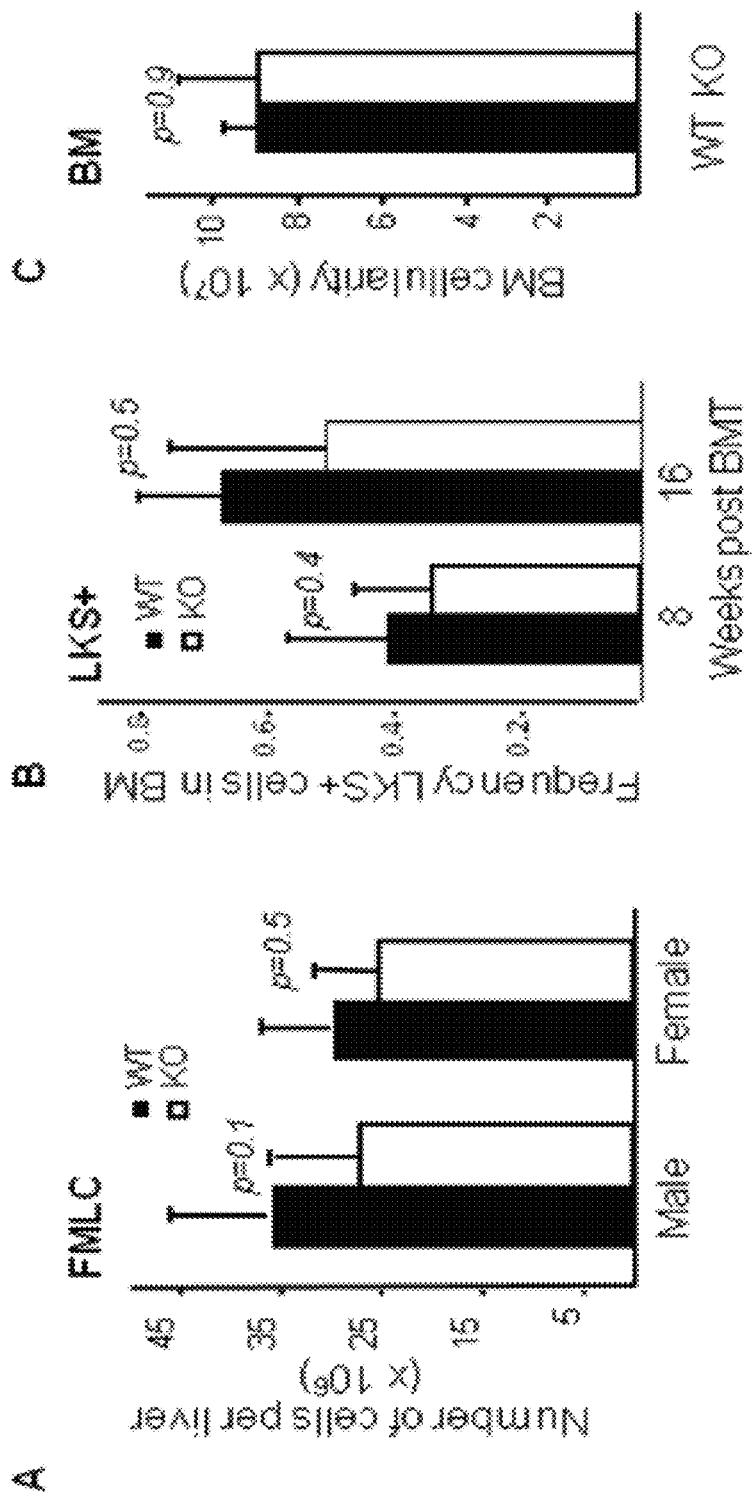
Figures 6A-C

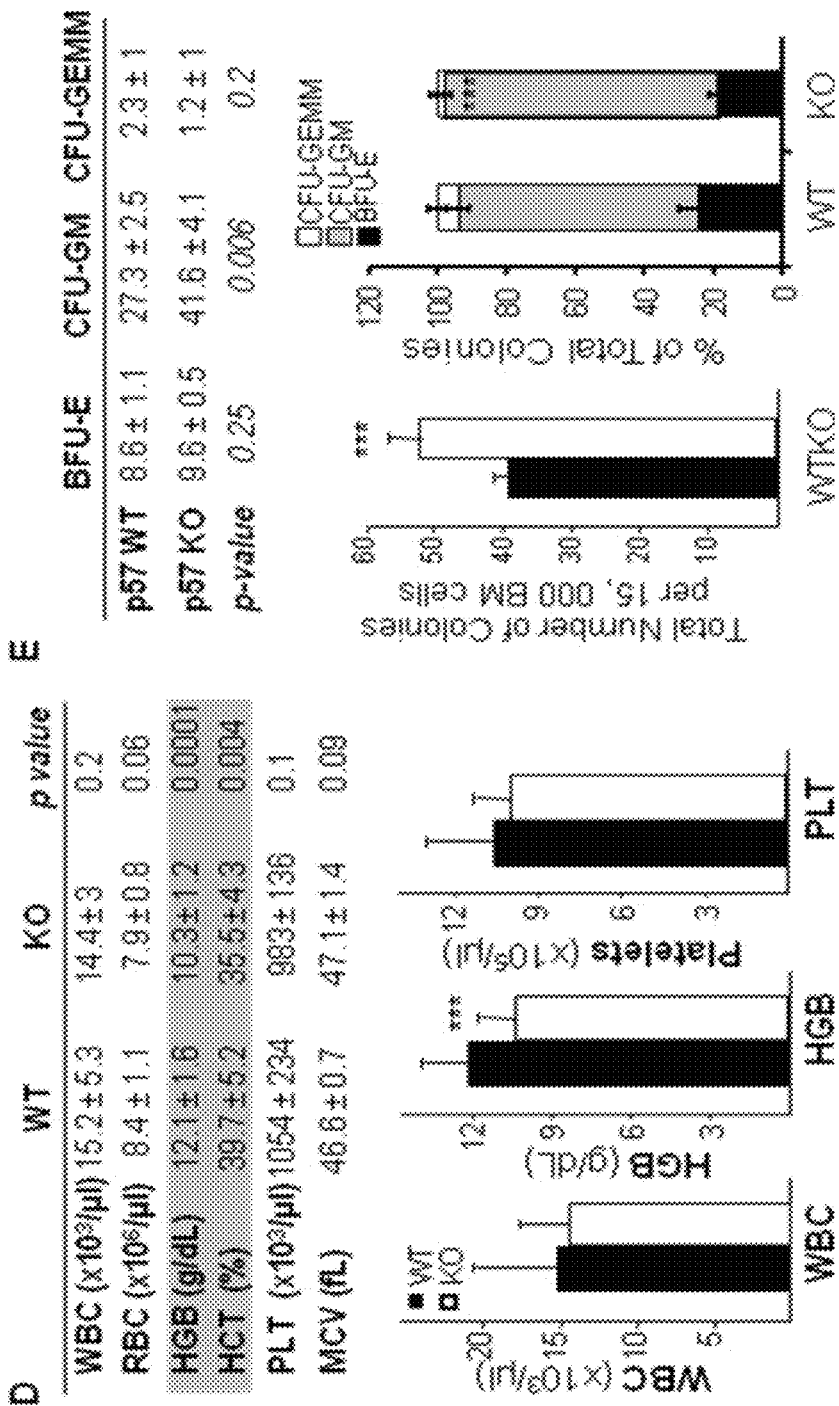
Figures 6D-E

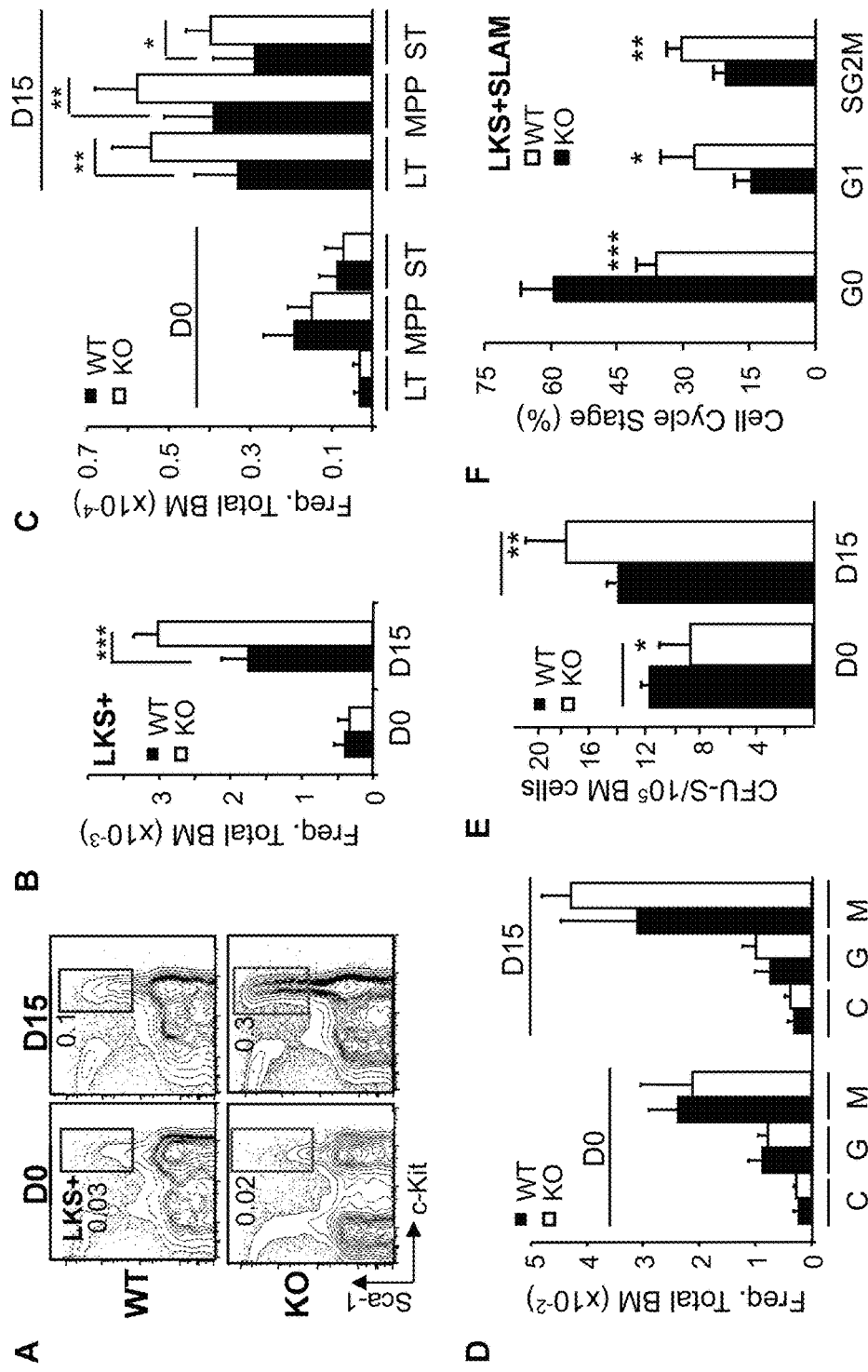
Figures 8A-F

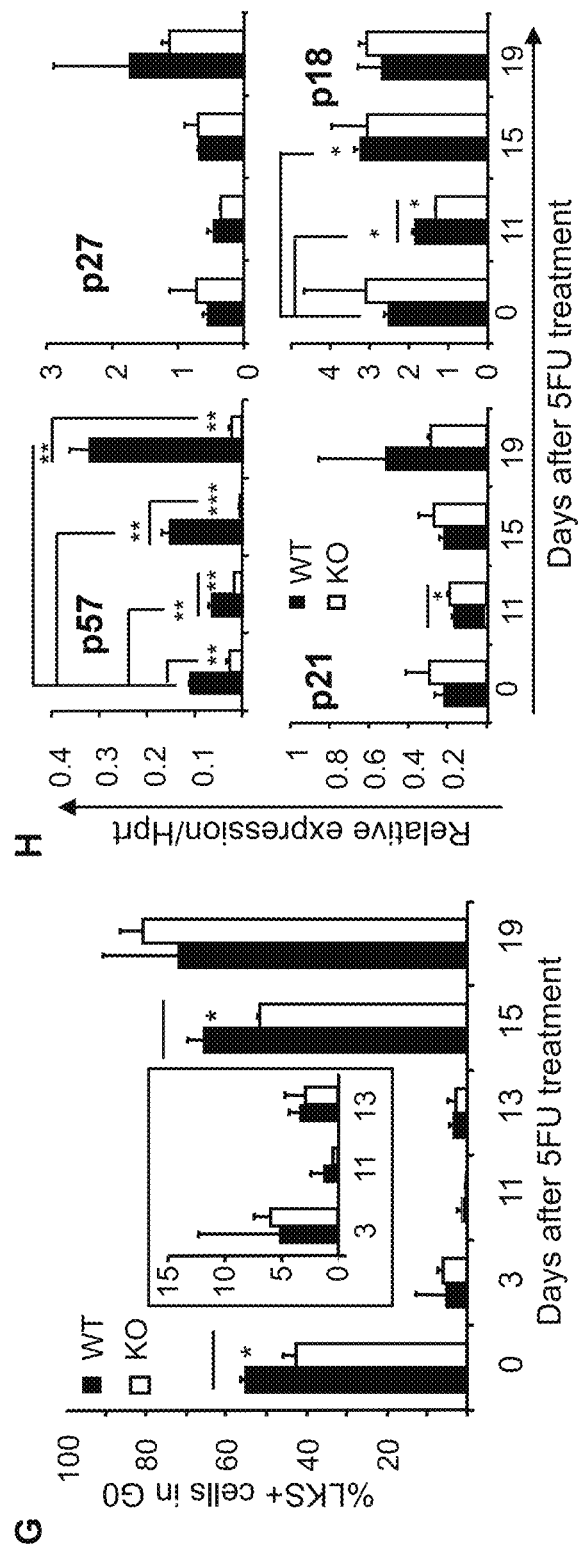
Figures 8G-H

SEQUENCE LISTING

<160> NUMBER OF SEQ ID NOS: 3

<210> SEQ ID NO 1
<211> LENGTH: 14
<212> TYPE: PRT
<213> ORGANISM: Artificial Sequence
<220> FEATURE:

```
<223> OTHER INFORMATION: Synthetic Peptide

<400> SEQUENCE: 1

Thr Gln His Ser Arg Val Leu Ser Leu Tyr Asn Thr Ile Asn
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Arg Val Leu Ser Leu
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 3

Cys Gly Gly Thr Gln Tyr Ser Lys Val Leu Ser Leu Tyr Asn Gln His
1               5                   10                  15
Asn
```

METHODS FOR STIMULATING HEMATOPOIETIC RECOVERY BY INHIBITING TGFβ SIGNALING

CROSS REFERENCE TO RELATED APPLICATIONS

This application claims priority from U.S. Provisional Application Nos. 61/562,766 filed Nov. 22, 2011, 61/579,447 filed Dec. 22, 2011, and 61/710,311 filed Oct. 5, 2012, the entire contents of each of which are incorporated herein by reference.

STATEMENT REGARDING FEDERALLY SPONSORED RESEARCH OR DEVELOPMENT

This invention was made with Government Support under Grant No. CA0104082 awarded by National Institutes of Health. The Government has certain rights in this invention.

INCORPORATION BY REFERENCE OF SEQUENCE LISTING

The Sequence Listing in an ASCII text file, named as 28275_5274_05_SequenceListing.txt of 2 KB, created on May 21, 2014, and submitted to the United States Patent and Trademark Office via EFS-Web, is incorporated herein by reference.

FIELD OF THE DISCLOSURE

This invention relates to methods for stimulating expansion and accelerating recovery of hematopoietic cells. More specifically, the methods disclosed herein are based on inhibition of TGFβ signaling and are useful for restoring normal levels of hematopoietic cells in subjects having reduced or deficient levels of hematopoietic cells as a result of hematologic stress, for example, myelosuppressive chemotherapy.

BACKGROUND ART

Hematopoietic stem cells (HSCs) are required for lifelong blood cell production and, to prevent exhaustion, the majority of HSCs are deeply quiescent during steady-state hematopoiesis. Paracrine factors produced by specialized bone marrow niche cells maintain HSC quiescence. During times of hematologic stress, HSCs are rapidly recruited into cell cycle and undergo extensive self-renewal and differentiation to meet increased hematopoietic demands. A great deal is known about how HSCs are mobilized during these periods of stress. Proteolytic enzymes such as MMP-9, cathepsin G and elastase cleave the chemokines (e.g., CXCL12), cytokines (e.g., KITL) and adhesive interactions that retain HSCs in the niche and maintain their quiescence. Circulating cytokine levels increase in response to cytopenias, tissue injury and inflammation and this reinforces HSPC proliferation. Yet it is not known how these processes wind down to allow HSCs to withdraw from cell cycling and return to quiescence. TGFβ has also been shown to block cytokine-driven HSC cycling (Batard et al., *J Cell Sci* 113:383-390 (2000); Scandura et al., *Proc Natl Acad Sci USA* 101:15231-15236 (2004); Yamazaki et al., *Blood* 113:1250-1256 (2009)).

TGFβ is one of the most potent inhibitors of cytokine-driven HSC proliferation in vitro (Batard et al., *J Cell Sci* 113:383-390 (2000); Blank et al., *Leukemia* 25:1379-1388 (2011); Fortunel et al., *Hematol J* 1:126-135 (2000); Fortunel et al., *Blood* 96:2022-2036 (2000); Scandura et al., *Proc Natl Acad Sci USA* 101:15231-15236 (2004); Sitnicka et al., *Blood* 88:82-88 (1996)), but its role in hematopoiesis has been harder to establish (Capron et al., *Blood* 116:1244-1253 (2010); Dickson et al., *Development* 121:1845-1854 (1995); Larsson et al., *Blood* 102:3129-3135 (2003); Larsson et al., *Exp Hematol* 33:592-596 (2005); Larsson et al., *Embo J* 20:1663-1673 (2001); Oshima et al., *Dev Biol* 179:297-302 (1996)). Identifying HSC defects in knockouts of TGFβ, or of its receptors Tgfbr1 (Alk5) and Tgfbr2, was difficult because the engineered mice develop a transplantable, lethal inflammatory disorder that largely prevents analysis of steady-state hematopoiesis in adult mice (Gorelik et al., *Immunity* 12:171-181 (2000); Letterio et al., *J Clin Invest* 98:2109-2119 (1996); Leveen et al., *Blood* 100:560-568 (2002); Yaswen et al., *Blood* 87:1439-1445 (1996)). Nonetheless, recent studies using a variety of elegant approaches to circumvent this lethal inflammatory disorder strongly suggest that TGFβ, signaling through Tgfbr2 and recruiting Smad4, is a putative niche factor that can maintain HSC quiescence during steady-state hematopoiesis (Blank et al., *Blood* 108:4246-4254 (2006); Karlsson et al., *J Exp Med* 204:467-474 (2007); Yamazaki et al., *Cell* 147:1146-1158 (2011); Yamazaki et al., *Blood* 113:1250-1256 (2009); Yamazaki et al., *Embo J* 25:3515-3523 (2006)).

SUMMARY OF THE DISCLOSURE

It has been shown herein that transforming growth factor-β (TGFβ) signaling is transiently activated in hematopoietic stem and progenitor cells (HSPCs) during hematopoietic regeneration, and that blockade of TGFβ signaling after a hematopoietic stress accelerates hematopoietic reconstitution and delays the return of cycling HSPCs to quiescence. Accordingly, this invention provides methods for stimulating hematopoietic regeneration by administering an inhibitor of TGFβ signaling to a subject having deficiencies in hematopoietic cells and/or recovering from a hematopoietic stress.

In one embodiment, a TGFβ signaling inhibitor is administered to a subject undergoing chemotherapy with a chemotherapeutic drug, such as anti-neoplastic drugs or antiviral drugs that are myelotoxic. In a specific embodiment, the TGFβ signaling inhibitor is administered to the subject after the administration of the chemotherapeutic drug, for example, one day or several days after the administration of the chemotherapeutic drug. In some embodiments, the timing of the administration of the TGFβ signaling inhibitor is determined based on monitoring the levels of mature blood cells in the subject. Use of a TGFβ signaling inhibitor permits chemotherapy with a higher dosing scheme (e.g., a higher dosage amount per dose, a more frequent dosing schedule, a longer treatment cycle, or a combination thereof), as compared to the dosing scheme without the TGFβ-pathway inhibitor.

In another embodiment, a TGFβ signaling inhibitor is administered to a subject undergoing hematopoietic stem cell transplant. The TGFβ signaling inhibitor can be administered after conditioning the subject with chemotherapy, radiation, and/or immunosuppressive agents.

In still another embodiment, a TGFβ signaling inhibitor is administered to a subject suffering an infection which causes hematopoietic stress and/or deficiencies, such as an infection which causes sepsis.

TGFβ signaling inhibitors as used herein include molecules which inhibit the level and/or activity of TGFβ, such as agents that block the upstream synthesis and activation of latent TGFβ to form active TGFβ, agents that block the interaction between TGFβ with its receptors, agents that inhibit the function or activity of TGFβ receptor, and agents that inhibit the downstream signaling cascade. TGFβ signaling inhibitors suitable for use in the present methods can be large molecule inhibitors (such as monoclonal antibodies, and soluble TGFβ antagonists such as polypeptides composed of the extracellular domain of a TGFβ receptor), antisense oligonucleotides, and small molecule organic compounds.

BRIEF DESCRIPTION OF THE DRAWINGS

FIG. 3. TGFβ limits HSPC proliferation after chemotherapy. (A) Representative multidimensional flow cytometry of BM cells prior to (D0) and after (D15) treatment with 5FU and 1D11 (D15-I) or the control antibody (D15-C). (B) Expansion of LKS (Lin$^-$ cKit$^+$Sca1$^+$) HSPCs, LKS$^+$Flk2$^-$CD34$^-$ (LT), LKS$^+$Flk2$^-$CD34$^+$ (ST), and LKS$^-$ FCRγII/IIIdimCD34$^+$ common myeloid progenitors (CMPs) was significantly greater in mice treated with 1D11 (grey bars, 5FU-I) during hematopoietic regeneration than in those treated with the control antibody (white bars, 5FU-C) (n=5). GMP, Granulocyte-Monocyte Progenitors; MEP, Megakaryocytes-Erythroid Progenitors. (C) Representative flow cytometry of LKS$^+$SLAM (LKS$^+$CD48$^-$CD150$^+$) on D15 post-5FU treatment and 1D11 (D15-I) or the control antibody (D15-C). (D) Colony Forming Cell (CFC) assay for committed hematopoietic progenitor cells showed more total colonies and CFU-GM in D15-I BM. Total, CFU-GM (Colony forming unit-granulocyte, macrophage) and erythroid-containing benzidine positive colonies are shown (n=3). All quantified data are shown as mean±SEM (*$p<0.05$, $p<0.01$, *$p<0.001$, or if undesignated, the comparison was not significant).

FIG. 6. p57-KO mice have a mild homeostatic phenotype. (A) The yield of FLMCs from p57-WT and p57-KO embryos is similar (n=10 for each genotype). FLMCs were transplanted into lethally irradiated (9 Gr) C57BL/6 recipients and once steady-state hematopoiesis was reached recipients were analyzed for (B) frequency of LKS+ HSPC in BM (n=5 for each genotype) and (C) BM cellularity. (D) Blood cell counts (n=20) between WT and KO-transplanted mice showed a mild normocytic anemia. WBC, white blood cells; RBC, red blood cells; HGB, Hemoglobin; HCT, Hematocrit; PLT, platelets. (E) Colony Forming Cell (CFC) assay for committed hematopoietic progenitor cells showed more total colonies and CFU-GM in the p57-KO BM. Total CFCs, CFU-GM (Colony forming unit-granulocyte, macrophage), CFU-GEMM (Colony forming unit-granulocyte, erythrocyte, macrophage, megakaryocyte), and BFU-E (Burst forming unit-erythroid) are presented in the graph (n=3 in triplicate for each genotype). All quantified data are shown as mean±SEM (*p<0.05, p<0.01, *p<0.001, or if undesignated, the comparison was not significant).

FIG. 8. p57-KO hematopoiesis phenocopies inhibition of TGFβ signaling during BM regeneration. (A) Representative multidimensional flow cytometry of p57-WT and p57-KO BM LKS cells prior to treatment (D0) or D15 after treatment with 5FU. (B-C) During hematopoietic regeneration (D15), p57-KO hematopoiesis had a more robust expansion of LKS (Lin−cKit+Sca1+) HSPCs, and LKS+Flk2−CD34− (LT), LKS+Flk2−CD34+ (ST), LKS+Flk2+CD34+ (MPP) subpopulations (n=5). (D) Recovery of CMP (C), GMP (G) and MEP (M) before (D0) and after (D15) chemotherapy was similar (n=5). (E) Expansion of immature MPPs was functionally validated using the colony forming unit spleen (CFU-S) assay (n=3). (F) Bi-dimensional cell cycle analysis shows that p57-KO LKS+SLAM cells remain in cycle longer than p57-WT HSCs during regeneration. (G) The population of quiescent LKS+ HSPCs prior to treatment (D0) and at various times after treatment with 5FU is shown. (H) Expression of p57, p21, p18 and p27 mRNA in Lin− BM cells of p57-WT and p57-KO recipients was assessed by qRT-PCR before and after chemotherapy administration. Expression was normalized to Hprt1 at each time point (n=3). The inventors identified no difference in the basal expression (homeostatic) of any gene but p57. All quantified data are shown as mean±SEM (*p<0.05, p<0.01, *p<0.001, or if undesignated, the comparison was not significant).

DETAILED DESCRIPTION

Figure 1:
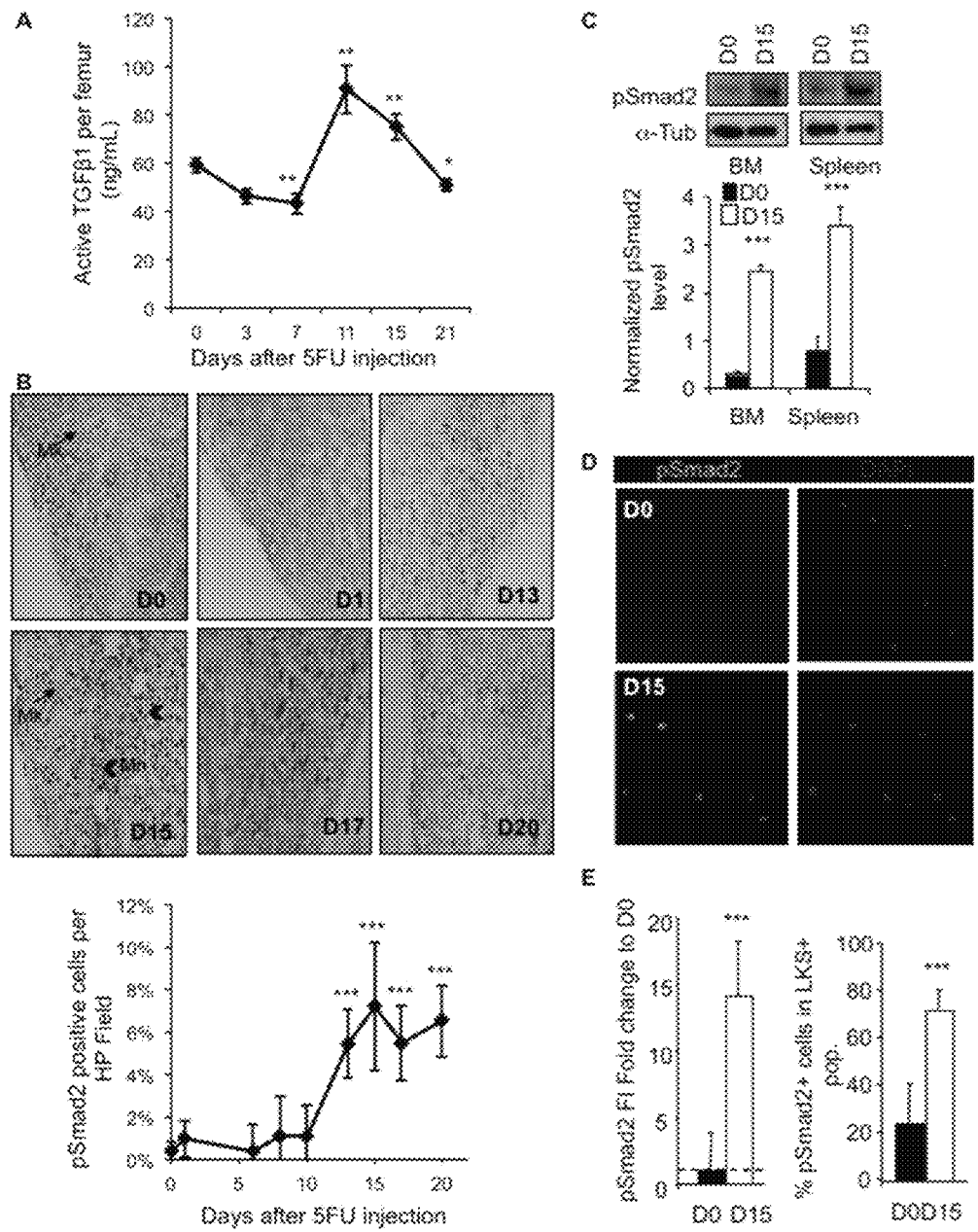
FIG. 1. TGFβ is activated during BM recovery from chemotherapy. (A) WT mice (n=16) were treated with a single dose of 5FU (250 mg/kg, i.p.) on D0. Measurement of active TGFβ in the bone marrow was performed before (D0) and at the indicated times after 5FU treatment. (B) (Upper panel) Immunohistochemical staining for pSmad2 was performed on BM sections collected before and after chemotherapy. Sections were counterstained with the nuclear stain, methyl green, to assess cellularity (original magnification, ×200). (Lower panel) Quantification of pSmad2 positive cells per High Power (HP) field at the indicated times after chemotherapy. (C) (Upper panel) Representative immunoblot of pSmad2 in Lin$^-$ BM and spleen cells during homeostasis (D0) and during recovery from chemotherapy (D15). (Lower panel) Replicate blots were quantified using ImageJ and pSmad2 was normalized to the α-tubulin loading control (n=3). (D) Expression of pSmad2 is upregulated in LKS$^+$ HSPCs on D15. FACS-purified LKS HSPCs were stained for pSmad2 (green) and DAPI (blue). (E) pSmad2 fluorescence intensity (FI) was quantified using ImageJ software. The D15/D0 FI ratio (left) and the percentage of pSmad2$^+$ HSPCs are shown at D0 and D15 (right). All quantified data are shown as mean±SEM (***$p<0.001$).

It has been demonstrated in this disclosure that transforming growth factor-β (TGFβ) signaling is transiently activated in hematopoietic stem and progenitor cells (HSPCs) during hematopoietic regeneration, and that blockade of TGFβ signaling after a hematopoietic stress (e.g., chemotherapy, transplantation, and infection) accelerates hematopoietic reconstitution and delays the return of cycling hematopoietic stem and progenitor cells (HSPCs) to quiescence. TGFβ blockade in these settings promotes multilineage hematopoietic regeneration by prolonging HSPC cycling and by promoting HSC self-renewal.

Model of Physiologic Contribution of TGFβ Signaling During Hematopoietic Regeneration. Homeostasis: At steady-state, most HSCs are maintained in a quiescent state by niche factors. Early Stress: HSCs are mobilized from the niche and actively cycle throughout early regeneration. Early Regeneration: Cytopenias persist and HSPCs actively cycle to repopulate the BM. Late Regeneration: Ordinarily, TGFβ is activated during late regeneration and this re-imposes HSPC quiescence. Transient blockade of TGFβ permits HSPCs to undergo additional rounds of division while the inhibitor concentration wanes. In the absence of p57, the cytostatic activity of TGFβ is delayed but eventually other TGFβ targets re-establish quiescence.

Methods of Hematopoietic Stimulation

In one aspect, this invention provides methods for stimulating hematopoietic regeneration by administering an inhibitor of TGFβ signaling to a subject having deficiencies in hematopoietic cells and/or recovering from a hematopoietic stress.

"Hematopoietic cells" as used herein include all types of blood cells from the myeloid (monocyte, macrophases, neutrophils, basophils, eosinophils, erythrocytes, platelets and dendritic cells) and lymphoid lineages (T-cells, B-cells and NK-cells).

"Hematopoietic stem cells (HSCs)" are multipotent stem cells that give rise to all types of blood cells. HSCs have the ability to replenish all blood cell types (multipotency) and the ability to self-renew. LT-HSCs are "long-term" HSCs that give rise to all blood types throughout the lifetime of an organism. ST-HSCs, which are derived from HSCs, have all the properties of LT-HSCs but only for a limited period of time.

"Hematopoietic progenitors", which are derived from HSCs, give rise to selected blood cell types. They have limited replicative potential and burn out after a few days-weeks.

The term "HSPCs" as used herein is an abbreviation referring to both hematopoietic stem cells and hematopoietic progenitor cells.

The term "deficiencies in hematopoietic cells" or "hematopoietic deficiencies", as used herein, means that the level(s) of one or more hematopoietic cell types or the combined level of hematopoietic cells is lower than normal. A "normal" level, as used herein can be a level in a control population, preferably a population of subjects having similar characteristics as the subject being treated, such as age. The "normal" level can also be a range of values. For example, the normal range is about 1800-7250/µl (mean ~3650) for neutrophils, 0-150/µl (mean ~30) for basophils, 0-700/µl (mean ~150) for eosinophils, 200-950/µl (mean ~430) for macrophages and monocytes, 1500-4000/µl (mean ~2500) for lymphocytes; $4.2 \times 10^6$-$6.1 \times 10^6$/µl for erythrocytes; and $133 \times 10^3$-$333 \times 10^3$/µl for platelets.

Hematopoietic deficiencies can arise from various hematologic stresses. For example, most chemotherapy (involving a cytotoxic compound, an immunosuppressive drug, or a steroid drug, for example) is associated with myelotoxicity, i.e., a slowdown of bone marrow function to produce hematopoietic cells. Other hematologic stresses include radiation therapy, hematopoietic stem cell transplantation, bleeding or other causes of blood cell loss or destruction (e.g., hemolysis, immune-mediated thrombocytopenia), and infection (e.g., infections that trigger sepsis).

By blocking or inhibiting TGFβ signaling, the hematopoietic deficiencies resulting from hematologic stress can be ameliorated and compensated by stimulated hematopoietic regeneration; in other words, multilineage hematopoietic reconstitution is promoted or accelerated by prolonging HSPC cycling and by promoting self-renewal. The stimulation is reflected by, e.g., increased self renewal and regeneration of hematopoietic stem cells (HSCs) and cells derived therefrom, including LT-HSCs (LKS+, CD34−, Flk2−), ST-HSCs, and progenitors cells, and/or delay in re-establishment of quiescence in HSCs (e.g., by at least 1, 2, 3, 4 days or longer).

The present methods can be used to treat any mammalian subject, including humans, nonhuman primates, companion animals (such as dogs, cats), horses, cows, pigs, sheep, among others.

In some embodiments, inhibition of TGFβ signaling is utilized to treat myelotoxic side effects of chemotherapy.

As described above, most chemotherapy is associated with myelotoxicity, a slowdown of bone marrow function to produce hematopoietic cells and concomitant reduction of mature blood cells. By "treating" the myelotoxic side effects of chemotherapy, the extent of myelotoxicity caused by chemotherapy is reduced, as reflected by, e.g., a quicker recovery of levels of white blood cells, red blood cells and platelets, as a result of an increased self renewal and regeneration of hematopoietic stem cells and/or delay in re-establishment of quiescence in HSCs.

The findings provided herein clearly establish TGFβ as a major regulator of hematopoietic stress serving to re-establish normal HSC quiescence through upregulation of p57. Therefore, TGFβ blockade should facilitate the delivery of traditional cytotoxic chemotherapeutics by reducing or ameliorating dose-limiting myelosuppression. Thus, a TGFβ-pathway inhibitor can be used as an adjunctive therapeutic to a traditional chemotherapeutic drug. Moreover, the use of a TGFβ-pathway inhibitor permits higher dosing of a traditional chemotherapeutic drug. By "higher dosing" is meant a higher amount per dose, a more frequent dose administration, and/or a longer cycle of dose administration, as compared to a dosing scheme of the chemotherapeutic drug without the a TGFβ-pathway inhibitor.

Generally speaking, the present approach of TGFβ signaling inhibition is applicable to treating myelotoxicity of any chemotherapeutic drug or a combination of drugs, including especially those developed for treating cancer, particularly solid tumors, such as breast cancer, esophagus cancer, nasopharynx cancer, colon cancer, rectum cancer, pancreas cancer, lung cancer, and prostate cancer. Examples of chemotherapeutic drugs for treating cancers include, but not limited to, Capecitabane (Xeloda), Carboplatin (Paraplatin), Cisplatin (CDDP), Cisplatin (Platinol), Cyclophosphamide (Cytoxan), Cytarabine, Docetaxel (Taxotere), Doxorubicin (Adriamycin), Etoposide (VePesid), Floxuridine (FUDR), 5-flurouracil, Gemcitibine, Ifosfamide (Ifex) Iressa, Irinotecan (Camptosar), Mitomycin (Mutamycin) Navelbine, Oxaliplatin (Eloxatin), Paclitaxel (Abraxane), Paclitaxel (Taxol), Pemetrexed (Alimta) Temozolomide, Topotecan (Hycamtin). Examples of combinations of chemotherapeutic drugs for treating cancers include Leucovorin/Floxuridine/Cisplatin/Mitomycin, Pemetrexed/Cisplatin/Cetuximab, Docetaxel/Carboplatin, Docetaxel/Carboplatin, Pemetrexed/Cisplatin, Leucovorin/Floxuridine, Cetuximab/Irinotecan, Pemetrexed/Cisplatin, Docetaxel/Carboplatin, Paclitaxel/Carbolplatin, Leucovorin/Floxuridine/Topotecan, Leucovorin/Floxuridine/Topotecan, Leucovorin/Floxuridine/Cetuximab/Mitomycin, Leucovorin/Floxuridine/Cisplatin/Mitomycin, Leucovorin/Floxuridine/Cisplatin/Mitomycin, Leucovorin/Floxuridine/Oxaliplatin, Docetaxel/Carboplatin/Pemetrexed/Cisplatin, Docetaxel/Carboplatin, Cetuximab/Irinotecan, Doxorubicin/Cyclophosphamide, Docetaxel/Carboplatin, Pemetrexed, Capecitabane, Capecitabane/Oxaliplatin/Irinotecan, Docetaxel, Etoposide/Trastuzumab/Zoledronic Acid/Carboplatin/Mesna/Ifosfamide, and Leucovorin/Floxuridine/Cisplatin/Mitomycin. TGFβ-pathway inhibitors can also be used in treatments involving non-antineoplastic chemotherapeutic drugs which are myelotoxic, such as antiviral drugs (e.g., anti-HIV drugs). An example of non-antineoplastic chemotherapeutic compounds which can cause myelosuppression is gancyclovir, an anti-viral drug. Functional derivatives of a drug, i.e., derivatives that maintains the desired pharmacological effect of the drug, can also be used in practicing the present invention, such as salts, esters, amides, prodrugs, active metabolites, analogs and the like. The exact combinations, doses, timing and route of the administration of the chemotherapeutic drugs can be determined by the treating oncologist using standard procedures (e.g., by considering Body Surface Area calculations).

A TGFβ-pathway inhibitor can be administered at various times during chemotherapy, including simultaneously with or after the administration of a chemotherapeutic drug. In some embodiments, a TGFβ-pathway inhibitor is administered after the administration of a chemotherapeutic drug, for example, at 1, 2, 3, 4, 5, 6, 7, 8, 9, 10 days or more after the administration of the chemotherapeutic drug. The TGFβ-pathway inhibitor can be administered one time after a chemotherapeutic drug, or multiple times (for example, on day 3 and day 5 after the administration of a chemotherapeutic drug).

It may be desirable to monitor the levels of mature blood cells in the subject after the administration of a chemotherapeutic drug, and time the administration of a TGFβ-pathway inhibitor based on the levels of mature blood cells. For example, the levels of mature blood cells can be monitored periodically (for example, daily, every other day, weekly, biweekly or monthly) and a TGFβ-pathway inhibitor is administered once the level(s) of one or more blood cell types is reduced as compared to thresholds or reference values, which can be predetermined levels from normal individuals or the level of the subject prior to chemotherapy. The term "mature blood cells" refers to fully differentiated hematopoietic cells such as those found in blood. In some embodiments, the blood cell type being monitored is one or more of red blood cells, platelets, white blood cells, and/or subtypes of white blood cells (e.g., neutrophils).

Other drugs that are beneficial to a patient undergoing chemotherapy can also be used. For example, the drugs Neupogen® or Neulasta®, which support the levels of white blood cell populations (e.g. neutrophils), can also be used. Such additional beneficial drugs can be administered simultaneously with a TGFβ signaling inhibitor, or with the chemotherapeutic drug or drugs; or alternatively, can be administered separately.

In other embodiments, inhibition of TGFβ signaling is utilized to treat hematopoietic deficiencies in subjects undergoing tissue or organ transplantation. For example, inhibition of TGFβ signaling in subjects after hematopoietic stem cell transplantation can be used to promote hematopoietic engraftment and blood count recovery. In this context, a TGFβ signaling inhibitor can be administered to the subject in conjunction with or after the administration of a transplant conditioning therapy (for example, chemotherapy, immunosuppressive drugs, and/or radiation therapy). In specific embodiments, a TGFβ-pathway inhibitor is administered after the administration of a transplant conditioning therapy, for example, at 1, 2, 3, 4, 5, 6, 7, 8, 9, 10 days or more after the conditioning regimen. The TGFβ-pathway inhibitor can be administered one time, or multiple times (for example, on day 3 and day 5 after the administration of an immunosuppressive drug). It may be desirable to monitor the levels of blood cells and determine the timing and dose of a TGFβ-pathway inhibitor based on the levels measured.

In still other embodiments, inhibition of TGFβ signaling is utilized to treat a subject with hematopoietic deficiencies resulting from an infection with a microorganism (e.g., bacteria or virus), such as an infection that triggers sepsis in a subject.

"TGFβ Pathway Inhibitors" or "TGFβ Signaling Inhibitors"

"TGFβ pathway inhibitors", "TGFβ signaling inhibitors", or "TGFβ inhibitors", as used herein, refer to molecules which inhibit the signal transduction mediated by TGFβ. TGFβ signaling inhibitors include molecules which inhibit the level and/or activity of TGFβ, such as agents that block the upstream synthesis and activation of latent TGFβ to form active TGFβ; agents that block the interaction between TGFβ with its receptors, and agents that inhibit the downstream signaling cascade, such as molecules which inhibit the level and/or activity of downstream targets of TGFβ signaling, for example, p57, among others (including those in the Smad-dependent pathway of TGFβ signaling). TGFβ-pathway inhibitors also include molecules that inhibit the function or activity of TGFβ receptors. See, e.g., Nagaraj and Datta, *Exp. Opin. Investig. Drugs* 19(1): 77-91 (2010); Korpal and Yang, *Eur J Cancer* 46: 1232-1240 (2010); and Akhurst et al., *Nature Reviews* 11:791 (2012); all of which are incorporated herein by reference in entirety.

TGFβ signaling inhibitors suitable for use in the present methods include large molecule inhibitors (such as monoclonal antibodies, and soluble TGFβ antagonists such as polypeptides composed of the extracellular domain of a TGFβ receptor), antisense oligonucleotides, and small molecule organic compounds.

In some embodiments, a large molecule TGFβ-pathway inhibitor is used in the present methods, which includes antibodies, antibody derivatives and antigen-binding antibody fragments that antagonize TGF-β ligand binding to TGF-β receptors. Examples of such antibodies are disclosed, for example, in U.S. Pat. No. 7,723,486, and EP 0945464, the entire contents of which are incorporated by reference. Such antibodies, derivatives and fragments thereof can be generated against one, two, or all TGF-β isoforms (i.e., TGF-β1, TGF-β2, and/or TGF-β3) or against one or more TGF-β receptors (e.g., TGF-βRI, TGF-βRII, and/or TGF-βRIII). Antibodies are preferentially generated against the regions of TGF-β or TGF-β receptors that are involved in ligand binding and/or signal transduction. Preferred TGF-β epitopes for binding include amino acids 56 to 69 of TGF-β2 (TQHSRVLSLYNTIN; SEQ ID NO: 1) with a three amino acid (CGG) extension at the N-terminus, even more preferably amino acids 60 to 64 of TGFβ2 (RVLSL, SEQ ID NO: 2). Other useful epitopes include amino acids 56 to 69 of TGFβ1 (CGG-TQYSKVLSLYNQHN; SEQ ID NO: 3).

Specific examples of suitable antibodies include Lerdelimumab (CAT-152) (Cambridge Antibody Technology) (Mead et al., *Invest Ophthalmol Vis Sci* 44(8):3394-3401 (2003)), Metelimumab (CAT-192) (Cambridge Antibody Technology) (Benigni et al., *J Am Soc Nephrol* 14(7):1816-

1824 (2003)), GC-1008 (Genzyme Corp. and Cambridge Antibody Technology) (Lahn et al., *Expert Opin Investig Drugs* 14(6):629-643 (2005)), ID11 (Genzyme Corp.) (Nam et al., *Cancer Res* 66(12):6327-35 (2006)), SR-2F (National Cancer Institute) (Lahn et al. (2005), supra), and 2G7 (Genentech Inc.) (Muraoka-Cook et al., *Clin Cancer Res* 11(2):937s-943s (2005)), all of which reviewed by Nagaraj et al., *Expert Opinion Investig Drugs* 19(1): 77-91 (2010); LY2382770 (Eli Lilly); IMC-TR1, an anti-TGFβRII blocking antibody (ImClone LLC) (ClinicalTrials.gov, NCT01646203); and STX-100 (Stromedix), an antibody that blocks aVβ6 integrins that are believed to be involved in the activation of latent TGFβ. See, also, review by Akhurst et al., *Nature Reviews* 11:791 (2012).

Various methods for the preparation of antibodies are known in the art (see, Antibodies: A Laboratory Manual, CSH Press, Eds., Harlow, and Lane (1988); Harlow, Antibodies, Cold Spring Harbor Press, NY (1989)). For example, a TGF-β or a TGF-β receptor or a fragment thereof can be administered to a recipient mammal to generate an immune response. Polyclonal as well as monocolonal antibodies that are specific for the TGF-β or TGF-β receptor can be generated from such an immunized mammal. For example, monoclonal antibodies specific for TGF-β or TGF-β receptor protein may be prepared, for example, using the technique of Kohler and Milstein, *Eur. J. Immunol.* 6:511-519, 1976, and improvements thereto.

Antibodies that bind specifically to TGF-β or TGF-β receptor protein can also be produced by recombinant means, including recombinantly produced chimeric and humanized antibodies. Humanized or human antibodies are preferred for use in therapeutic contexts to avoid unwanted immunogenicity caused by antibody molecules. Methods for humanizing murine and other non-human antibodies, by substituting one or more of the non-human antibody sequences for corresponding human antibody sequences, are well documented in the art (see for example, Jones et al., *Nature* 321: 522-525 (1986); Riechmann et al., *Nature* 332: 323-327 (1988); Verhoeyen et al., *Science* 239: 1534-1536 (1988), Carter et al., *Proc. Natl. Acad. Sci. USA* 89: 4285 (1993); and Sims et al., *J. Immunol.* 151: 2296 (1993)). Fully human monoclonal antibodies of the invention can be generated using cloning technologies employing large human Ig gene combinatorial libraries (i.e., phage display) (Griffiths and Hoogenboom, *Building an in vitro immune system: human antibodies from phage display libraries*. In: Protein Engineering of Antibody Molecules for Prophylactic and Therapeutic Applications in Man, Clark, M. (Ed.), Nottingham Academic, pp 45-64 (1993); Burton and Barbas, *Human Antibodies from combinatorial libraries*. Id., pp 65-82). Fully human monoclonal antibodies of the invention can also be produced using transgenic mice engineered to contain human immunoglobulin gene loci (see also, Jakobovits, *Exp. Opin. Invest. Drugs* 7(4): 607-614 (1998); U.S. Pat. No. 6,162,963 issued 19 Dec. 2000; U.S. Pat. No. 6,150,584 issued 12 Nov. 2000; and U.S. Pat. No. 6,114,598 issued 5 Sep. 2000).

Specificity and affinity of an antibody for TGF-β or TGF-β receptor can be assessed by many techniques known in the art. For example, the specificity may be determined by ELISA. Wells of a multi-well plate are coated with TGF-β or TGF-β receptor protein, using methods known in the art. Anti-TGF-β or TGF-β receptor protein antibodies are added, and reactivity with TGF-β or TGF-β receptor protein is determined by antibody binding affinity. Other means of determining specificity, well known to those of skill in the art, include FACS analysis and immunochemistry.

Antibody formulations of the invention are administered via any route capable of delivering the antibodies to a patient. Routes of administration include, but are not limited to, intravenous, intraperitoneal, intramuscular, intratumor, intradermal, and the like. Typically, an antibody is given at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg antibodies per week are effective and well tolerated.

In other embodiments, the TGF-β signaling inhibitor is a soluble TGFβ antagonist such as a polypeptide composed of the extracellular domain of a TGFβ receptor (referred to by some as "ligand trap"). Examples of soluble TGFβ antagonists include TGF-βRII:Fc (a stabilized soluble protein from Biogen Idec; see Muraoka et al., *J Clin Invest* 109(12):1551-1559 (2002)), and betaglycan/TGF-βRIII (a recombinant soluble protein comprising the extracellular domain of the TGF-β3 receptor; see Bandyopadhyay et al., *Cancer Res* 59(19):5041-5046 (1999)), both reviewed by Nagaraj et al. (2010, supra).

In other embodiments, the TGF-β signaling inhibitor is an oligonucleotide inhibitor, such as but not limited to antisense oligonucleotides, RNAi, dsRNA, siRNA and ribozymes. Such antisense oligonucleotides antagonize TGF-β signaling.

As used in the specification, "antisense oligonucleotide" refers to a stretch of single-stranded DNA or RNA, usually chemically modified, whose sequence (3'-5') is complementary to the sense sequence of a molecule of mRNA. Antisense molecules thereby effectively inhibit gene expression by forming RNA/DNA duplexes, and offer a more targeted option for cancer therapy than chemotherapy or radiation. Antisense is believed to work by a variety of mechanisms, including physically blocking the ability of ribosomes to move along the messenger RNA, and hastening the rate at which the mRNA is degraded within the cytosol.

The antisense oligonucleotide may be a 5-10-5 gap-mer methoxyl ethyl modified (MOE) oligonucleotide corresponding to the sequence of a TGF-β isoform. The antisense oligonucleotides according to the present invention are typically between 7 and 100 nucleotides in length. In one embodiment, the antisense oligonucleotides comprise from about 7 to about 50 nucleotides, or nucleotide analogs. In another embodiment, the antisense oligonucleotides comprise from about 7 to about 35 nucleotides, or nucleotide analogs. In other embodiments, the antisense oligonucleotides comprise from about 12 to about 35 nucleotides, or nucleotide analogs, and from about 15 to about 25 nucleotides, or nucleotide analogs. In one embodiment, this oligonucleotide has a phosphorothioate backbone throughout.

It is understood in the art that an antisense oligonucleotide need not have 100% identity with the complement of its target sequence in order to be effective. The antisense oligonucleotides in accordance with the present invention, therefore, have a sequence that is at least about 70% identical to the complement of the target sequence. In one embodiment of the present invention, the antisense oligonucleotides have a sequence that is at least about 80% identical to the complement of the target sequence. In other embodiments, they have a sequence that is at least about 90% identical or at least about 95% identical to the complement of the target sequence, allowing for gaps or mismatches of several bases. Identity can be determined, for example, by using the BLASTN program of the University of Wisconsin Computer Group (GCG) software.

In order for the antisense oligonucleotides of the present invention to function in inhibiting TGF-β, it is desirable that they demonstrate adequate specificity for the target sequence and do not bind to other nucleic acid sequences in the cell. Therefore, in addition to possessing an appropriate level of sequence identity to the complement of the target sequence, the antisense oligonucleotides for use in the present invention should not closely resemble other known sequences. The antisense oligonucleotides of the present invention, therefore, should be less than 50% identical to any other mammalian nucleic acid sequence.

Specific examples of antisense oligonucleotides useful as TGFβ signaling inhibitors include AP-12009 (Antisense Pharma) (Schlingensiepen et al., *Recent Results Cancer Res* 177:137-150 (2008)), AP-11014 (Antisense Pharma) (Saunier et al., *Curr Cancer Drug Targets* 6(7):565-578 (2006)), and NovaRx (NovaRx) (Lahn et al., *Expert Opin Investig Drugs* 14(6):629-643 (2005)), as reviewed by Nagaraj et al., *Expert Opinion Investig Drugs* 19(1): 77-91 (2010), all the above publications incorporated herein by reference.

Inhibition of TGF-β may also be achieved using RNA interference or "RNAi". RNAi or double-stranded RNA (dsRNA) directs gene-specific, post-transcriptional silencing in many organisms, including vertebrates. RNA interference mediated by siRNAs is known in the art to play an important role in post-transcriptional gene silencing (Zamore, *Nature Struc. Biol.*, 8:746-750, 2001). In nature, siRNA molecules are typically 21-22 base pairs in length and are generated when long double-stranded RNA molecules are cleaved by the action of an endogenous ribonuclease. RNAi may be effected via directly introducing into the cell, or generating within the cell by introducing into the cell a suitable precursor (e.g. vector, etc.) of such an siRNA or siRNA-like molecule. An siRNA may then associate with other intracellular components to form an RNA-induced silencing complex (RISC). Transfection of mammalian cells with synthetic siRNA molecules having a sequence identical to a portion of a target gene leads to a reduction in the mRNA levels of the target gene (Elbashir et al., *Nature*, 411:4914498, 2001).

Oligonucleotide TGF-β inhibitors can be siRNA molecules that are targeted to a TGF-β ligand or receptor gene such that the sequence of the siRNA corresponds to a portion of said gene. RNA molecules used in the present invention generally comprise an RNA portion and some additional portion, for example a deoxyribonucleotide portion. The total number of nucleotides in the RNA molecule is typically less than 49 in order to be effective mediators of RNAi. In some embodiments, the number of nucleotides is 16 to 29, and in some specific embodiments, 18 to 23, and in other specific embodiments 21-23. In certain embodiments of the invention, the siRNA or siRNA-like molecule is less than about 30 nucleotides in length. In a further embodiment, the siRNA or siRNA-like molecules are about 21-23 nucleotides in length. In an embodiment, siRNA or siRNA-like molecules comprise and 19-21 bp duplex portion, each strand having a 2 nucleotide 3' overhang. In certain embodiments of the invention, the siRNA or siRNA-like molecule is substantially identical to a TGF-β-encoding nucleic acid or a fragment or variant thereof. The double-stranded siRNA molecules can further comprise poly-T or poly-U overhangs at the 3' and 5' ends to minimize RNase-mediated degradation of the molecules. Design and construction of siRNA molecules is known in the art (see, for example, Elbashir, et al, *Nature* 411:494498, 2001; Bitko and Barik, *BMC Microbiol.*, 1:34, 2001). In addition, kits that provide a rapid and efficient means of constructing siRNA molecules by in vitro transcription are also commercially available (Ambion, Austin, Tex.; New England Biolabs, Beverly, Mass.).

The present invention further contemplates use of ribozyme oligonucleotide inhibitors of TGFβ signaling. Ribozymes are RNA molecules having an enzymatic activity that enables the ribozyme to repeatedly cleave other separate RNA molecules in a nucleotide-sequence specific manner. Such enzymatic RNA molecules can be targeted to virtually any mRNA transcript, and efficient cleavage can be achieved in vitro (Kim et al., *Proc. Natl. Acad. Sci. USA*, 84:8788, 1987; Haseloff and Gerlach, *Nature,* 334:585, 1988; Cech, *JAMA,* 260:3030, 1988; Jefferies et al., *Nucleic Acids Res.,* 17:1371, 1989). Typically, a ribozyme comprises two portions held in close proximity: an mRNA binding portion having a sequence complementary to the target mRNA sequence, and a catalytic portion which acts to cleave the target mRNA. A ribozyme acts by first recognizing and binding a target mRNA by complementary base-pairing through the target mRNA binding portion of the ribozyme. Once it is specifically bound to its target, the ribozyme catalyzes cleavage of the target mRNA. Such strategic cleavage destroys the ability of a target mRNA to direct synthesis of an encoded protein. Having bound and cleaved its mRNA target, the ribozyme is released and can repeatedly bind and cleave new target mRNA molecules.

In further embodiments, the TGFβ signaling inhibitor utilized in the methods of this invention is a small molecule, synthetic or naturally occurring organic compound. As used herein, a small molecule compound is defined as a molecule of less than 1200 Daltons, preferably less than 1000 Daltons, or preferably less than 800 Daltons.

Examples of suitable small molecule TGFβ-pathway inhibitors include LY-550410 (Eli Lilly) (Yingling et al., *Nat Rev Drug Discov* 3(12):1011-1022 (2004)), LY-580276 (Eli Lilly) (Sawyer, *Curr Med Chem Anticancer Agents* 4(5): 449-455 (2004)), LY-364947 (Eli Lilly) (Sawyer et al., *J Med Chem* 46(19):3953-3956 (2003)), LY-2109761 ((Eli Lilly) (Sawyer, *Curr Med Chem Anticancer Agents* 4(5): 449-455 (2004)), LY-2157299 (Eli Lilly) (Yingling et al., *Nat Rev Drug Discov* 3(12):1011-1022 (2004)), LY-573636 (Eli Lilly), SB-505124 (GlaxoSmithKline) (Saunier et al., *Curr Cancer Drug Targets* 6(7):565-578 (2006)), SB-431542 (GlaxoSmithKline) (Hjelmeland et al., *Mol Cancer Ther* 3(6):737-745 (2004)), GW788388 (GlaxoSmithKline), SD-208 (Scios Inc.) (Uhl et al., *Cancer Res* 2004; 64(21):7954-7961 (2004)), SD-093 (Scios Inc.) (Subramanian et al., *Cancer Res* 64(15):5200-5211 (2004)), Ki-26894 (Kirin Brewery Co.) (Ehata et al., *Cancer Sci* 98(1):127-133 (2007)), Sm16 (Biogen Idec; see also Suzuki et al., *Cancer Res* 67(5):2351-2359 (2007)), NPC-30345 (Scios Inc.) (Dumont et al., *Cancer Cell* 2003; 3(6):531-6 (2003)), A-83-01 (Kyoto Pharma) (Tojo et al., *Cancer Sci* 96(11):791-800 (2005)), SX-007 (Scios Inc.) (Tran et al., *Neuro Oncol* 9(3):259-70 (2007)), IN-1130 (In2Gen Co.) (Moon et al., *Kidney Int* 70(7):1234-1243 (2006)), and pyrrole-imidazole polyamide. See, also, Akhurst et al., *Nature Reviews* 11:791 (2012).

Additional exemplary small molecule TGFβ-pathway inhibitors include compounds having the following generic formula, as disclosed in U.S. Pat. No. 7,087,626 (to Eli Lilly, incorporated herein by reference):

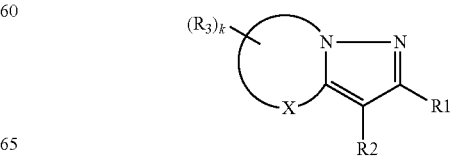

or the formula as U.S. Pat. No. 7,087,626 (to Eli Lilly, incorporated herein by reference):

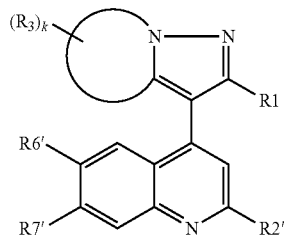

or another formula disclosed in U.S. Pat. No. 7,087,626 (to Eli Lilly, incorporated herein by reference):

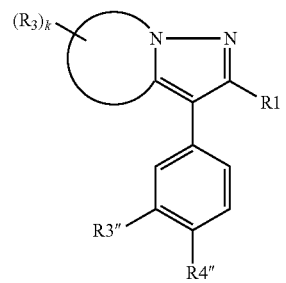

or yet another formula disclosed in U.S. Pat. No. 7,087,626 (to Eli Lilly, incorporated herein by reference):

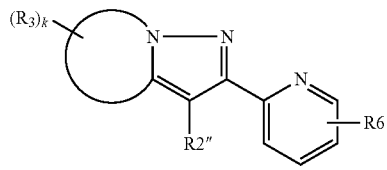

A particular example of a TGFβ-pathway inhibitor compound LY2157299, is disclosed in U.S. Pat. No. 7,265,225 (to Eli Lilly, incorporated herein by reference):

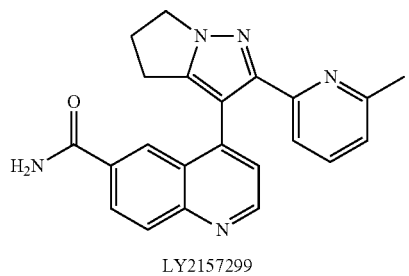 [SMILES: Cc1cccc(-c2nn3c(c2-c2ccnc4ccc(C(N)=O)cc24)CCC3)n1]

LY2157299

Other exemplary small molecule TGFβ-pathway inhibitors include compounds with the following generic formula as disclosed in U.S. Pat. No. 6,476,031 (to Scios Inc., incorporated herein by reference):

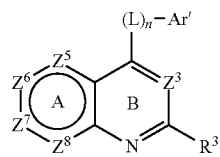

or the pharmaceutically acceptable salts thereof.

A particular example of a compound of this formula, SD-093, is disclosed in U.S. Pat. No. 6,476,031 (to Scios Inc.):

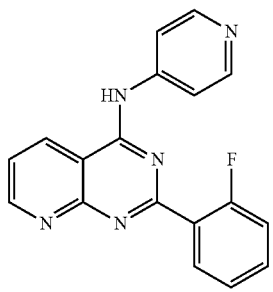

SD-093

Another example is SD-208 (Scios) having the formula:

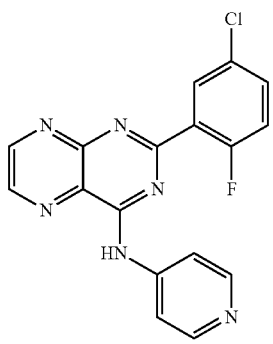

SD208 (Scios)

Other exemplary small molecule TGFβ-pathway inhibitors include compounds as disclosed in U.S. Pat. No. 7,407,958, in particular the compound IN-1130:

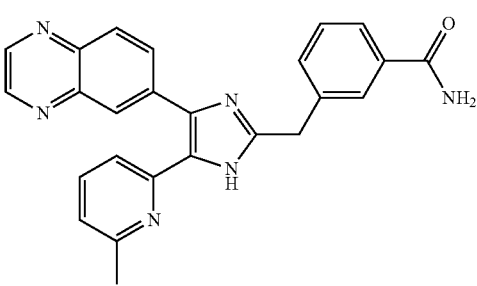

IN-1130

Other exemplary small molecule TGFβ-pathway inhibitors include compounds as disclosed in U.S. Pat. No. 7,053,095 (Pfizer Inc.), in particular the compound:

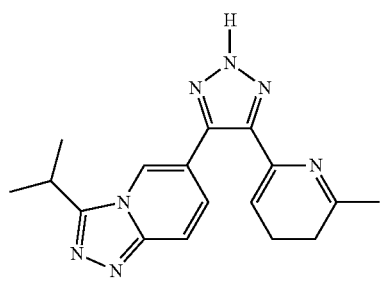 [SMILES: CC1=NC(c2n[nH]nc2-c2ccc3nnc(C(C)C)n3c2)=CCC1]

Other exemplary small molecule TGFβ-pathway inhibitors include, but are not limited to, compounds with the following formulas:

Additional inhibitors described by Nagaraj (2010, supra) and Akhurst (2012, supra) also suitable for use herein include Trx-xFoxH1b and Trx-Lefl (Smad-interacting peptide aptamers) (Cui et al., *Oncogene* 24(24):3864-3874 (2005)), Distertide (p144) (a peptide based on TβRII that blocks ligand binding to receptors, from Digna Biotech), p17 (peptide derived from phage display that targets TGFβ1 binding to receptor, from Digna Biotech), LSKL (a peptide based on thrombospondin and specifically blocks TGFβ activation).

Administration and Dose

A suitable TGFβ-pathway inhibitor can be combined with one or more pharmaceutically acceptable carriers for administration. As used herein, a pharmaceutically acceptable carrier includes any and all solvents, dispersion media,

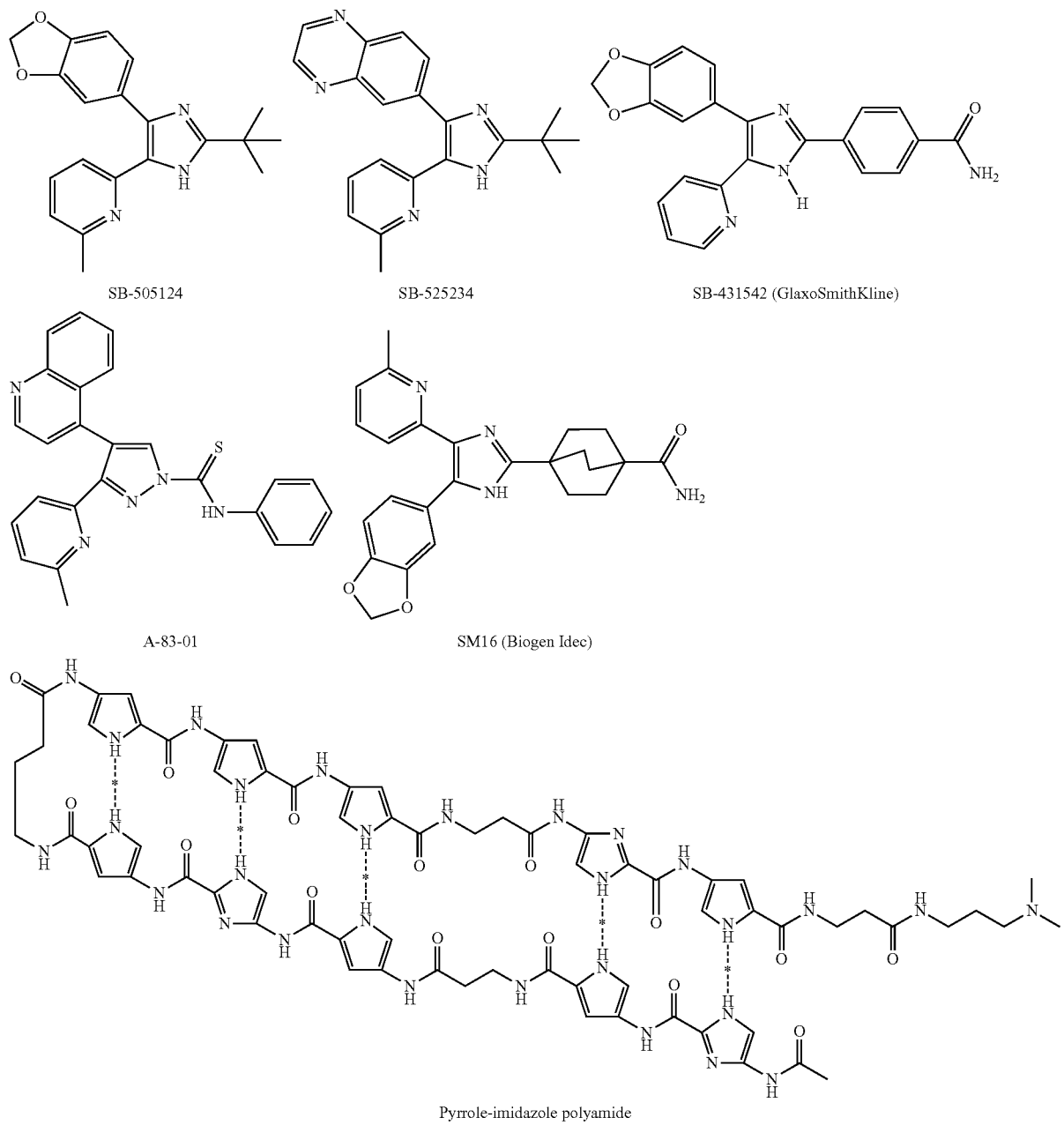

isotonic agents and the like. Except insofar as any conventional media, agent, diluent or carrier is detrimental to the recipient or to the therapeutic effectiveness of the TGFβ-pathway inhibitor or the chemotherapeutic drug, its use in practicing the methods of the present invention is appropriate. The carrier can be liquid, semi-solid, e.g. pastes, or solid carriers. Examples of carriers include water, saline solutions, alcohol, sugar, gel, oils, lipids, liposomes, resins, porous matrices, binders, fillers, coatings, preservatives and the like, or combinations thereof. In accordance with the present invention, the active ingredients can be combined with the carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like.

According to the present invention, a suitable TGFβ-pathway inhibitor can be administered to a patient via various routes, including the sublingual, oral, parenteral (e.g., intravenous, intraperitoneal, intradermal, subcutaneous or intramuscular) route.

Generally speaking, the daily dose of a suitable TGFβ-pathway inhibitor will be dictated by its mode of action, pharmacokinetics and pharmacodynamics. The precise dose can be determined by the treating physician, taking into consideration of the patient's blood cell levels, the route of administration and other physical parameters such as age, weight and overall well being. In specific embodiments, the patient is given a dose daily or at other intervals sufficient to block TGFβ signaling in hematopoietic cells when administered at specified times (for one or more days) after the administration of a chemotherapeutic drug, or at multiple times on the specified days.

The present description is further illustrated by the following examples, which should not be construed as limiting in any way. The contents of all cited references (including literature references, issued patents, and published patent applications as cited throughout this application) are hereby expressly incorporated by reference.

Example-1

This Example describes materials and methods used in the following examples.

Animals

Mice with targeted disruption of the p57 gene (Zhang et al., *Nature* 387:151-158 (1997)) were backcrossed into C57BL/6J (The Jackson Laboratory, Bar Harbor, Me.). Mice with homozygous deletion of p57 (i.e., p57$^{-/-}$ or p57-KO mice) or with a maternally-inherited p57-targeted allele (p57+/−m) are not viable but embryos survive to at least day 20 (E20) allowing FLMCs to be harvested from viable embryos. To facilitate analysis of HSC-transplant recipient mice, the inventors crossed p57 mice with transgenic mice expressing EGFP under control of the ubiquitin C promoter (Schaefer et al., *Cell Immunol* 214:110-122 (2001)). Hematopoietic cells from these mice express EGFP in all blood lineages. Animals were maintained in Weill Cornell Medical College Animal Facility according to IACUC-approved protocol.

Immunophenotypic Analysis of BM HSPCs and HSCs by Flow Cytometry.

Mice were killed by $CO_2$ asphyxiation and femur, tibia and humeri were dissected free of muscle and tendons and then crushed in DMEM using a mortar and pestle. The resulting cell suspension was filtered through a 70-µm filter and washed in PEB (2 mM EDTA, 0.2% BSA in PBS pH 7.4). Spleens were isolated and then minced prior to grinding through a 70-µm filter to generate single cell suspensions. Lineage negative (Lin$^-$) cells were purified using a biotinylated lineage cell detection cocktail (Miltenyi Biotec). Lineage depleted cells were then stained with streptavidin-Qdot 605 (eBioscience), Horizon V450-conjugated anti-CD117 (BD Biosciences), PECy7-conjugated Sca-1 (BioLegend), Alexa700-conjugated CD34 (BD Biosciences), APC-conjugated CD135 (Flk2) (BioLegend), and PerCP/Cy5.5-conjugated CD16/32 (FcR). Hematopoietic populations were identified as following: LT-HSCs, LKS$^+$ CD34$^-$Flk2$^-$; ST-HSCs, LKS$^+$ CD34$^+$ Flk2$^-$; MPPs, LKS$^+$ CD34$^+$ Flk2$^+$; CMPs, LKS$^-$ CD34$^+$ FcRlow; GMPs, LKS$^-$ CD34$^+$ FcR$^+$; and MEPs, LKS$^-$ CD34$^-$ FcR$^-$ MEPs. DAPI was used to exclude dead cells during flow cytometric analysis. To identify LKS$^+$SLAM cells, lineage depleted cells were stained with APC-conjugated CD117 (BD Biosciences), PECy7-conjugated Sca-1 (BioLegend), Alexa 700-conjugated CD48 (BioLegend) and PE-conjugated CD150 (BioLegend). To analyze cell cycle, lineage depleted cells were stained with streptavidin-PE (BioLegend), APC-conjugated CD117 (BD Biosciences), PECy7-conjugated Sca-1 (BioLegend) and then fixed and permeabilized using CytoFix/Perm (BD Bioscience) prior to staining with PerCP/C5.5-conjugated Ki67 (BD Bioscience) and Hoechst 33342 (Invitrogen). The cell cycle status of LKS$^+$SLAM cells was analyzed using this same strategy. Analysis gates were set based upon the fluorescence minus one (FMO) fluorophore. Multidimensional FACS analysis was performed using a BD LSRII equipped with 5 lasers (Beckton-Dickinson). FlowJo was used to analyze flow cytometry data (Tree Star, Inc.).

Stem and Progenitors Cell Assays

Primitive myeloid progenitors were enumerated using the day 12 CFU-S assay. Briefly, recipient mice were irradiated and injected with $1 \times 10^5$ bone marrow cells. Spleens were isolated 12 days post-transplantation and fixed in Bouin's solution. The number of macroscopic spleen colonies were counted and expressed as the number of CFU-S colonies per $1 \times 10^5$ donor cells. Clonogenic myeloid progenitors were assessed by standard methylcellulose colony forming cell assays (MethoCult GF M3434, Stem Cell Technologies) using $1.5 \times 10^4$ bone marrow mononuclear cells (BMMCs) per well (6-well plate). Colonies were scored after 10 days of incubation and expressed as the number of CFUs per $1.5 \times 10^4$ BMMCs.

Bone Marrow Transplantation

Mice were irradiated with 9 Gy using a $^{137}$Cs-γ-ray source. Three to four hours after lethal irradiation, FLMCs or BMMCs from donor animals were injected into the tail vein of recipient animals. For serial bone marrow transplantation, BMMC ($2 \times 10^6$ cells) from 10 animals of each genotype were individually transplanted into lethally irradiated mice. Eight to twelve weeks after engraftment, BMMCs were harvested from the transplanted recipients and used as donor cells for the next set of lethally irradiated recipients. This procedure was repeated sequentially. Competitive repopulation (CRU) assay was performed by mixing either p57-WT or p57-KO test FLMCs (EGFP$^{+/+}$) with the same number of control FLMCs from congenic CD45.1$^{+/+}$ pups. The 1:1 (test/competitor) mixture ($1 \times 10^6$ cells total) was injected into lethally irradiated mice via tail vein (n=10). Peripheral blood was analyzed by flow cytometry at various times after reconstitution for the presence of p57-WT or p57-KO CD45.2$^{+/+}$, EGFP$^{+/+}$ cells test cells and EGFP$^{-/-}$ CD45.1$^{+/+}$ control cells.

To assess how TGFβ blockade during hematopoietic regeneration affects functional HSC activity, the inventors competitively transplanted WT recipient mice with mixtures of genetically marked cells (EGFP$^{+/+}$, CD45.2$^{+/+}$ or EGFP$^{-/-}$, CD45.1$^{+/+}$) isolated from the BM of mice treated with 5FU and then with either the TGFβ-neutralizing antibody 1D11 (I) or a non-targeted control antibody 13C4 (C) (see Myelosuppressive treatment and TGFβ inhibition). On D15, BM cells for each condition (D15-C or D15-I) were mixed 1:1 (2×10$^6$ cells total) and injected into lethally irradiated C57BL/6J mice via tail vein (n=10). Peripheral blood was analyzed for multilineage engraftment by flow cytometry at various times after transplantation. The origin of donor cells was identified by the EGFP, CD45.2, and CD45.1 staining profiles. To control for any influence of the genetic marker (none observed), the inventors performed the experiment in two cohorts: one with a mixture of EGFP$^{+/+}$-D15-I and CD45.1$^{+/+}$-D15-C BMMCs; and a second with a mixture of EGFP$^{+/+}$-D15-C and CD45.1$^{+/+}$-D15-I BMMCs.

Myelosuppressive Treatment

The inventors used 5FU (250 mg/kg, 1 i.p.) for C57BL/6J mice, or 5FU 150 mg/kg (1 i.p.) for mice that had been previously transplanted. To assess blood count recovery, the inventors collected peripheral blood (50 µl) into EDTA-coated capillary tubes (Fisher Scientific). Differential blood counts were measured using an automated Bayer ADVIA 120 Multispecies Hematology Analyzer calibrated for murine blood (Bayer HealthCare).

TGFβ Inhibition

The inventors treated cohorts of mice with 5FU (250 mg/kg) on day 0 and then with either the TGFβ-neutralizing antibody 1D11 (I) (10 mg/kg) or a non-targeted control antibody 13C4 (C) (10 mg/kg) on days 5, 7 and 9. The 1D11 and 13C4 antibodies were generously provided by Genzyme Corp., Framingham, Mass., USA. Mice were treated with 5FU (250 mg/kg) on day 0 and then received either LY364947 (1 mg/kg, i.p.) or an equal volume of PBS six times over a period of 9 days. Hematopoietic reconstitution was followed by monitoring peripheral blood counts and multidimensional flow cytometry on bone marrow and spleen cells, as indicated.

Other Hematologic Stressors

To induce hemolysis, C57BL/6J mice or chimeric mice stably engrafted with p57-WT or p57-KO FLMCs were injected with phenylhydrazine hydrochloride (PHZ) (60 mg/kg, i.p) (Sigma-Aldrich) on D1 and D2. To assess the function of TGFβ signaling, C57BL/6J mice were treated 20 with either the TGFβ-neutralizing antibody 1D11 (I) (10 mg/kg) or a non-targeted control antibody 13C4 (C) (10 mg/kg) on D3 and D4 after PHZ. Mice were sacrificed on D8 for analysis. As a model of massive infection, C57BL/6J mice were injected with lipopolysaccharides (LPS) (2 mg/kg, i.p.) (Sigma-Aldrich) and then with either I or C, 6 hours after LPS and sacrificed on D3 and D4 for analysis. To assess the effect of TGFβ blockade on HSC function after transplantation, the inventors lethally irradiated mice (9 Gy) and then transplanted them with 2×10$^6$ BM cells from 8 week old C57BL/6J donor mice. Then, the inventors injected recipient mice with either I or C every 2 to 3 days between D5 and D14 after transplantation. Mice were sacrificed on D19 for analysis. The effect of these treatments on the return of HSCs to quiescence was assessed by analyzing the bivariate cell cycle of LKS-SLAM cells isolated from the BM of recipient mice.

Bone Marrow Homing

BM cells were harvested from donor chimeric mice engrafted with EGFP+/+p57-WT or p57-KO hematopoiesis. Recipients were conditioned by lethal irradiation and then transplanted with 10 million donor BM cells. Lodgement and engraftment of donor cells was analyzed at 2, 24 and 48 hours after transplantation. Recipients were killed by $CO_2$ asphyxiation and donor LKS+ cells were identified in recipient BM by flow cytometry.

TGFβ Measurement

Mice were killed by $CO_2$ asphyxiation and the femurs were dissected free of muscle and tendons and then crushed in PEB (2 mM EDTA, 0.2% BSA in PBS pH 7.4) using a mortar and pestle. The resulting cell suspension was filtered through a 70-µm filter and remaining particulates were removed by centrifugation. The clarified supernatant was used to quantify total and active TGFβ1 by ELISA (R&D Systems) following manufacturer instructions.

IHC and IF

Femurs were fixed in 4% paraformaldehyde (PFA) overnight and then decalcified using 10% EDTA prior to freezing in OCT (Sakura Finetek, Calif.). Immunohistochemical staining was performed on frozen sections using anti-pSmad2 (Millipore) and anti-p57 (Epitomics) antibodies. The specificity of staining was assessed in sequential sections using non-targeted, species matched, primary antibodies in place of the pSmad2 or p57 antibodies. After blocking endogenous peroxidase with 0.1% hydrogen peroxide, sections were incubated in primary Abs overnight at 4° C., followed by signal amplification utilizing Avidin-Biotin horseradish peroxidase complex method (ABC Vectastain, Vector Labs). The time used for color development was fixed for all conditions. Sections were briefly counterstained with MethylGreen (Vector Laboratories). Staining was quantified by collecting images from 20 high-power fields per masked slide. The images were then analyzed by two blinded reviewers. For immunofluorescence staining, cells were sorted using a 5-laser FACSAria II Special Research instrument (BD Bioscience) and collected onto Cell-Tak (BD Bioscience) coated coverslips prior to fixation with 4% PFA. Cells were permeabilized with 0.1% Triton X-100, blocked in PBS, 2% BSA, 5% Normal Donkey serum (NDS) and incubated overnight with pSmad2 (Santa Cruz) and/or p57 (Epitomics) antibodies. Cells were then stained with donkey anti-goat Alexa-488 and/or donkey anti-rabbit Alexa-555 and counterstained with DAPI to reveal nuclei. Cover slips were mounted in 70% glycerol and images were collected using a Zeiss 710 laser scanning confocal microscope. For quantitative analysis of p57 and pSmad2 positive cells, fluorescence intensity was quantified using ImageJ software (Wayne Rasband, National Institutes of Health (NIH), MD, USA).

Immunoblotting

Bone marrow or spleen cells were depleted of lineage-expressing cells and then washed and pelleted prior to lysis in TBS containing 2 mM EDTA, 1× Laemmli Sample Buffer, 1% NP40, with phosphatase inhibitors (10 mM sodium fluoride, 1 mM sodium pyrophosphate) and protease inhibitor cocktail tablets (Roche, Indianapolis, Ind., USA). Samples were separated on 10% NuPAGE gels (Invitrogen), and transferred to polyvinylidene difluoride (PVDF) membranes (Millipore, Bedford, Mass., USA) prior to blocking with 5% non-fat dried milk in PBS with 0.1% Tween 20. Primary and secondary antibodies were diluted in blocking solution. Primary antibodies against p57 (Epitomics), p27 (BD transduction Labs), pSmad2 (Millipore) Smad 2/3 (generous gift of J. Massagué) and β-Actin (Cell Signaling) were used. Secondary peroxidase-conjugated anti-rabbit antibody (Calbiochem, USA) was used prior to chemiluminescent visualization using the SuperSignal West Femto Substrate (ThermoScientific). Signal intensities were quantified using ImageJ (Wayne Rasband, National Institutes of Health (NIH), MD, USA).

Quantitative Reverse Transcriptase PCR Analysis

Transcript expression was analyzed by reverse transcriptase quantitative PCR (qPCR) using a 7500 Fast Real-Time PCR System with a Taqman Fast Universal PCR master mixture (Applied Biosystems). Expression was normalized to Hprt1 (Mm00446968_m1). Standard curves were generated with FLMC RNA from WT mice. The following TaqMan Gene Expression Assay Mixes were used: p57 (Mm00438170_m1), p21 (Mm00432448_m1), p18 (Mm00483243_m1) and p27 (Mm00438168_m1).

Statistical Analysis

Student's t-test (two-tailed) was used to analyze the statistical differences between groups, with the p-values indicated in the related graphs. All data are expressed as mean±SEM (n.s. non significant, *$p<0.05$, $p<0.01$, *$p<0.001$).

Example-2

This Example describes the results from experiments conducted to investigate the role of TGFβ signaling in establishing HSPCs homeostasis following chemotherapy.

TGFβ Signaling is Activated During Hematopoietic Recovery from Myelosuppression

To study hematopoietic recovery after chemotherapy, the inventors treated mice with the antimetabolite, 5-flurouracil (5FU), and measured TGFβ1 in the bone marrow (BM) during hematopoietic regeneration (FIG. 1A). 5FU targets cycling hematopoietic cells and causes extensive bone marrow (BM) aplasia with a nadir between D6 and D8 after chemotherapy. The level of active TGFβ initially declined slightly but then rose significantly as hematopoiesis was restored 11 to 15 days after chemotherapy. The inventors monitored phosphorylation of the intracellular mediator, Smad2 (pSmad2), to report intracellular activation of the TGFβ pathway. Whereas immunohistochemical (IHC) staining for pSmad2 was weak in homeostatic BM (5FU-D0), both the intensity and proportion of BM cells staining for pSmad2 increased during hematopoietic regeneration after chemotherapy (FIG. 1B). Smad2 phosphorylation peaked on D15 when the BM cellularity and blood counts were returning to normal. Western blots confirmed strong induction of TGFβ signaling on D15 in immature (not expressing mature lineage markers, Lin⁻) hematopoietic cells isolated from the marrow or spleen (FIG. 1C). The inventors sorted LKS HSPCs (Lin⁻, cKit⁺, Sca-1⁺) onto coverslips prior to and on D15 after a myelosuppressive dose of 5FU and used immunofluorescence (IF) staining and confocal microscopy to quantify relative pSmad2 expression (FIG. 1D). These results show that BM TGFβ was activated and its intracellular signaling was induced in HSPCs during late hematopoietic regeneration. Because TGFβ signaling was activated in HSPCs when hematopoiesis was being replenished, the inventors next tested whether blockade of this pathway would affect hematopoietic regeneration.

TGFβ Blockade after Chemotherapy Promotes Hematopoietic Regeneration.

Figure 2:
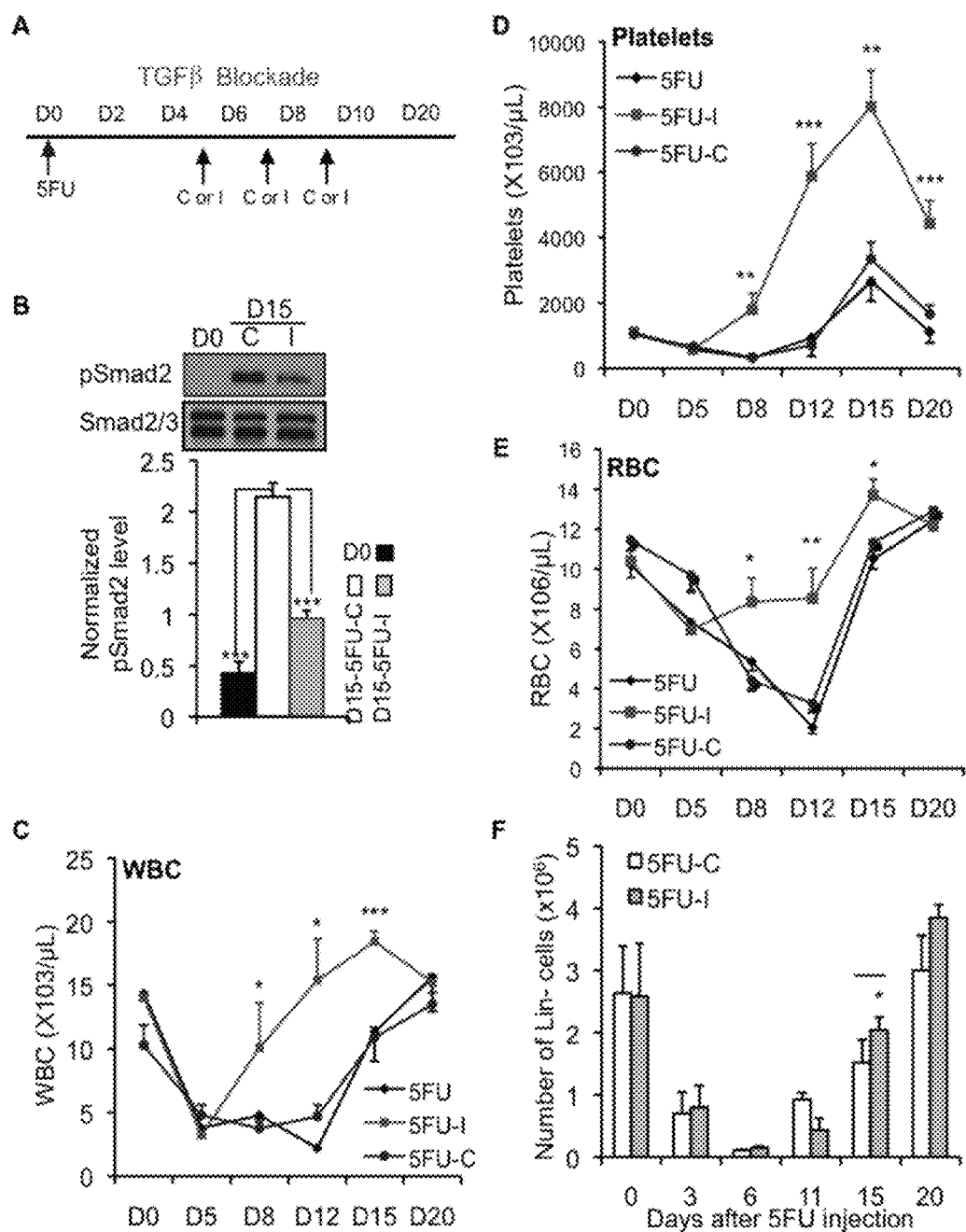
FIG. 2. Blockade of TGFβ during recovery from chemotherapy promotes hematopoietic regeneration. (A) Cohorts of mice were treated with 5FU on D0 and then with no additional agent (black line), the TGFβ-neutralizing antibody, 1D11 (red line, 5FU-I) (n=6), or a non-targeted isotype control antibody, 13C4 (blue line, 5FU-C) (n=6) on days 5, 7 and 9 (arrows). (B) (Upper panel) Representative immunoblot of pSmad2 in Lin$^-$ BM during homeostasis (D0) and during recovery from chemotherapy (D15) with 1D11 (I) or 13C4 antibody treatment. (Lower panel) Replicate blots were quantified using ImageJ and pSmad2 was normalized to the Smad2 band (upper) of the Smad 2/3 loading control (n=3). (C-F) Mice with neutralized TGFβ recovered white blood cells (WBC) (C), platelets (D), red blood cells (RBC) (E), and immature Lin$^-$ cells (F) significantly faster than did mice in either control group (n=6). All quantified data are shown as mean±SEM (*$p<0.05$, $p<0.01$, *$p<0.001$, or if undesignated, the comparison was not significant).

To assess how TGFβ signaling alters hematopoietic regeneration, the inventors administered myelosuppressive chemotherapy to mice and then, during recovery, treated cohorts with either an antibody that specifically neutralizes active TGFβ (1D11), an isotype control antibody (13C4), or nothing at all (control) (FIG. 2A). Inhibition of TGFβ signaling during regeneration by 1D11 was confirmed by Western blot of Lin⁻ cells before and D15 after chemotherapy (FIG. 2B). Multilineage hematopoiesis regenerated more quickly in mice treated with 1D11 than it did in either control group (5FU+I, FIG. 2C-E). Similarly, mice treated with a small molecule inhibitor of Tgfbr1 (LY364947) also recovered blood counts more rapidly than did mice treated with a vehicle control (FIG. 10A-G). The effect of TGFβ blockade could not result from altered chemotherapy cytotoxicity because the inhibitor was administered after the BM cellularity had already reached nadir. Since both myeloid and lymphoid lineages recovered faster in the mice treated with the TGFβ neutralizing antibody, the inventors reasoned that the accelerated recovery was likely a consequence of enhanced HSPC regeneration and indeed more Lin⁻ HSPCs were found during regeneration of the marrow in mice treated with the inhibitor (FIG. 2F). Notably, blockade of TGFβ in homeostatic BM did not increase blood cell counts or bone marrow cellularity, demonstrating that TGFβ signaling plays a key role during hematopoietic reconstitution. These studies suggest that context-dependent activation of the TGFβ pathway restrains hematopoietic regeneration after myelotoxic stress.

Context-Dependent TGFβ Signaling Restores HSPC Quiescence and Limits Self-Renewal after Chemotherapy.

To investigate the mechanisms by which TGFβ dampens hematopoietic recovery, we used polyvariate flow cytometry to analyze HSPC regeneration in mice treated with chemotherapy followed by either 1D11 or the 13C4 control antibody (FIG. 3A). Ordinarily, myelotoxic stress triggers self-renewal of HSCs coupled to expansion of hematopoietic progenitor cells (Morrison et al., *Proc Natl Acad Sci USA* 94:1908-1913 (1997); Passegue et al., *J Exp Med* 202:1599-1611 (2005); Wilson et al., *Cell* 135:1118-1129 (2008)). The inventors found greater expansion of LKS⁺ HSPCs, of enriched LKS⁺ subsets and of LKS-hematopoietic progenitors cells (HPCs) in mice treated with 1D11 (FIG. 3B). There were also more colony forming cells (CFCs) in the BM of mice that had TGFβ signaling blocked during regeneration after chemotherapy (FIG. 3D). To assess whether TGFβ blockade expanded bona fide HSCs with long-term repopulation potential relative to controls, the inventors performed competitive transplantation assays. The inventors isolated cells from the BM of D15-I and D15-C EGFP⁺/⁺ or CD45.1+/+ mice, mixed them in a 1:1 ratio and then competitively transplanted them into normal recipients. The inventors monitored the contribution of the engrafted cells to multilineage blood cells using flow cytometry and markers of donor cell source (CD45.1, CD45.2 and EGFP). Although initial engraftment was in the expected proportion, the contribution of D15-I cells progressively overtook that of D15-C cells. The time frame of the competitive advantage suggests that TGFβ blockade after chemotherapy promoted the expansion of HSCs with long-term repopulation potential. Therefore, in the absence of TGFβ, HSPCs undergo additional rounds of cell division during BM regeneration. Notably, regeneration of very immature LKS⁺SLAM (LKS⁺, CD150⁺, CD48⁻) cells—an immunophenotype highly enriched for HSCs during homeostasis and stress (Kiel et al., *Cell* 121:1109-1121 (2005); Yilmaz et al., *Blood* 107:924-930 (2006))—was also enhanced in mice treated with the TGFβ-neutralizing antibody (FIG. 3C). The inventors therefore reasoned that TGFβ might be directly involved in re-establishing HSPC quiescence.

Figure 4:
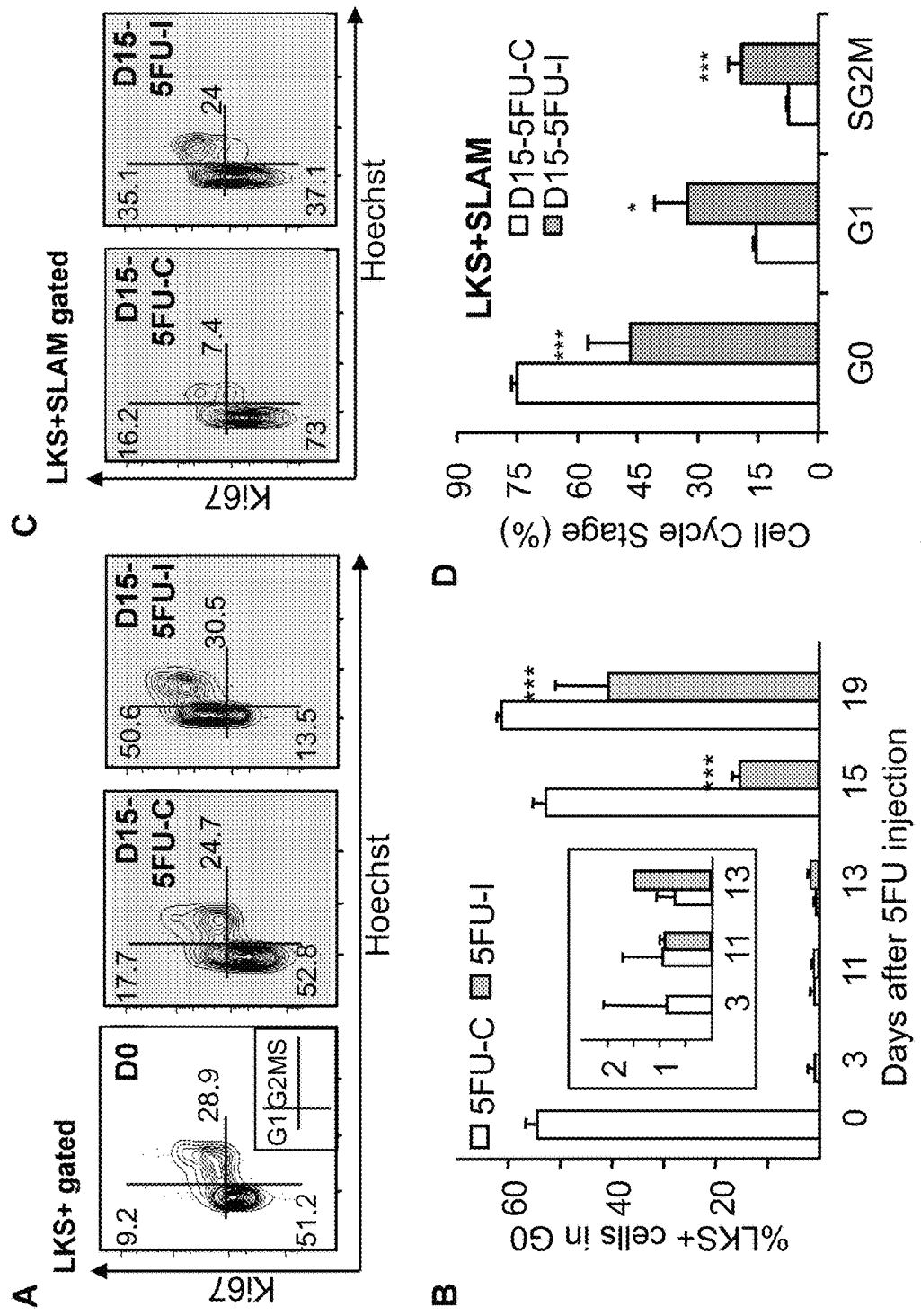
FIG. 4. Blockade of TGFβ during recovery from myelotoxic stress prolongs HSPC cycling. The inventors treated cohorts of mice with 5FU and then with either the TGFβ-neutralizing antibody, 1D11 (5FU-I), or an isotype control antibody, 13C4 (5FU-C) (n=5), on days 5, 7 and 9 after chemotherapy. (A) Representative bi-dimensional cell cycle status of BM LKS$^+$ HSPCs is shown prior to treatment (D0) and at various times after treatment with 5FU and 1D11 (5FU-I) or the control antibody (5FU-C). (B) The population of quiescent LKS cells prior to treatment (D0) and at various times after treatment with 5FU and 1D11 (I) or the control antibody (n=5). HSPCs normally return to quiescence by D15 (white and black bars) but persist in G1 if TGFβ signaling is blocked during BM regeneration (grey bars). (C) Representative bi-dimensional cell cycle status of BM LKS$^+$ SLAM HSCs at D15 after treatment with 5FU and 1D11 (5FU-I) or the control antibody. (D) Cell cycle status of BM LKS$^+$SLAM HSCs is shown at D15 after treatment with 5FU and 1D11 (5FU-I) or the control antibody (n=5). All quantified data are shown as mean±SEM (*$p<0.05$, $p<0.01$, *$p<0.001$, or if undesignated, the comparison was not significant).

The inventors explored the mechanism by which TGFβ blockade enhances hematopoietic regeneration and promotes HSC self-renewal by assessing the cell cycle status of HSPCs during recovery from myelosuppressive chemotherapy (FIG. 4). During steady-state hematopoiesis, most LKS⁺ and LKS⁺SLAM cells are quiescent and bi-dimensional cell cycle analysis identifies them in $G_0$ (2N DNA with no Ki67) (Passegue et al., *J Exp Med* 202:1599-1611 (2005)). Following a myelotoxic insult, virtually all LKS HSPCs quickly enter cell cycle and then continue to cycle until the BM begins to regenerate some time between D13 and D15. Although HSPCs normally return to quiescence at this point, the inventors found that TGFβ blockade permitted LKS⁻ HPCs, LKS⁺ HSPCs (FIG. 4A-B) and LKS⁺SLAM cells (FIG. 4C-D) to continue cycling for several more days. Similarly, mice treated with a small molecule inhibitor of Tgfbr1 (LY364947) after 5FU, also had prolonged cycling of these cell populations and also recovered blood counts more rapidly than did mice treated with a vehicle control (FIG. 10A-G). Thus, a previously unrecognized function of TGFβ is to re-establish HSC quiescence and restrain progenitor proliferation once hematopoiesis has sufficiently recovered from stress.

To test whether this function depends upon the circumstances of TGFβ blockade, the inventors administered the 1D11 (inhibiting) or the 13C4 (control) antibody to mice during homeostasis. Blockade of the TGFβ pathway in homeostatic BM failed to induce either LKS HSPCs or LKS⁺SLAM cells to emerge from quiescence. This finding suggests that the action of TGFβ in homeostatic BM differs from that during late hematopoietic regeneration when the levels of active TGFβ increase and its downstream signaling in HSPCs manifests. These results indicate that a central role of TGFβ is to re-establish quiescence in the context of BM regeneration.

TGFβ Induces Context-Dependent p57 Expression During Hematopoietic Regeneration.

Figure 5:
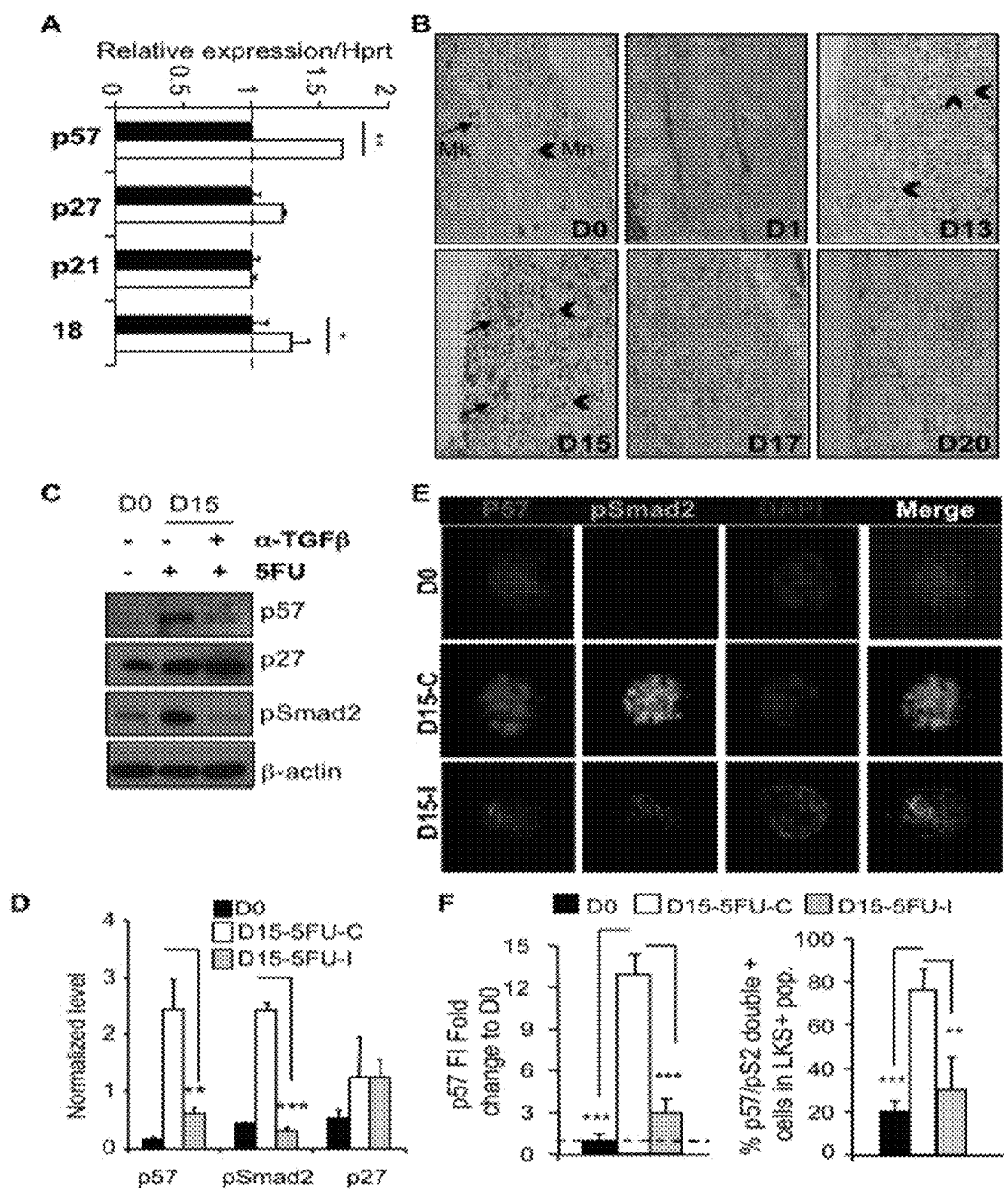
FIG. 5. TGFβ is required for p57 upregulation during recovery from myelosuppressive chemotherapy. (A) We used qRT-PCR to study the expression of CDKIs in Lin$^-$ BM cells of C57BL/6J mice before (D0) or after (D15) administration of 5FU (250 mg/kg, i.p.). Expression of p57, p21, p18 and p27 mRNA was normalized to Hprt1 at each time point (n=3). (B) Wild-type mice were killed before (D0) and at the indicated times after a single dose of 5FU chemotherapy. Femurs were stained for p57 and nuclei were counterstained with methylgreen. p57 staining was seen in both megakaryocytes (Mk, small arrows) and small mononuclear cells (Mn, large arrow heads). Expression of p57 (reddish-brown) and maximally upregulated D15 after 5FU treatment. (C) Cohorts of mice were treated with 5FU on D0 and then with the TGFβ-neutralizing antibody 1D11 or a non-targeted control antibody 13C4 on days 5, 7 and 9. Immunoblots for p57, pSmad2 and p27 in Lin$^-$ BM cells from mice homeostatic (D0) BM and D15 after chemotherapy show that 1D11 effectively blocked Smad2 phosphorylation and p57 upregulation whereas p27 expression was unaffected. (D) Replicate blots were quantified using ImageJ and expression normalized to β-actin (n=3). (E) LKS HSPCs were FACS purified from mice prior to (D0), and on D15 after 5FU chemotherapy followed by either 1D11 (D15I) or 13C4 (D15-C), as described previously. Purified cells were stained for p57 (red), pSmad2 (green) and for DNA using DAPI (blue). Images were acquired using a Zeiss 710 laser scanning confocal microscope and (F) fluorescence intensity (FI) was quantified using ImageJ software. All quantified data are shown as mean±SEM (*$p<0.05$, $p<0.01$, *$p<0.001$, or if undesignated, the comparison was not significant).

To identify how spatiotemporal activation of TGFβ signaling reinstates quiescence of cycling HSPCs, the inventors investigated the expression of cyclin-dependent kinase inhibitors (CKDNIs) that function in these cells (Cheng et al., *Nat Med* 6:1235-1240 (2000); Cheng et al., *Science* 287:1804-1808 (2000); Matsumoto et al., *Cell Stem Cell* 9:262-271 (2011); Scandura et al., *Proc Natl Acad Sci USA* 101:15231-15236 (2004); Yuan et al., *Nat Cell Biol* 6:436-442 (2004); Zou et al., *Cell Stem Cell* 9:247-261 (2011)). Of these CDKIs, only p57 and p18 were induced during the window of TGFβ activation (FIG. 5A). It was previously found that only p57—and not p18—was transcriptionally regulated by TGFβ in human HSPCs and identified p57 as a major downstream mediator of TGFβ-induced cytostasis in these cells (Scandura et al., *Proc Natl Acad Sci USA* 101:15231-15236 (2004)). Subsequent work has shown that p57 is highly expressed in deeply quiescent HSCs (CD34 LKS) positioning this CDKI in a cellular compartment where it could function as a gatekeeper of quiescence (Miyamoto et al., *Cell Stem Cell* 1:101-112 (2007); Qian et al., *Cell Stem Cell* 1:671-684 (2007); Yamazaki et al., *Blood* 113:1250-1256 (2009); Yamazaki et al., *Embo J* 25:3515-3523 (2006)). Indeed, p57 has been recently reported to help maintain HSC quiescence during homeostasis (Matsumoto et al., *Cell Stem Cell* 9:262-271 (2011); Zou et al., *Cell Stem Cell* 9:247-261 (2011)). The inventors therefore reasoned that p57 might also be a key effector of TGFβ serving to re-establish HSC quiescence during late hematopoietic regeneration after chemotherapy.

Immunohistochemical staining showed that the spatiotemporal pattern of p57 expression was similar to TGFβ pathway activation during BM regeneration (FIG. 5B). During homeostasis, p57 expression is restricted to large, polyploidy megakaryocytes (Mk) and small, uncommon mononuclear cells (Mn), presumably HSPCs. During recovery from chemotherapy, the number of small p57-expressing cells increases dramatically and is most prominent on D15. Western blots of immature Lin⁻ BM cells from 5FU-treated mice revealed strong upregulation on D15 of p57 and pSmad2 and to a far lesser extent of p27 (FIG. 5C-D). Both Smad2 phosphorylation and p57 expression were blocked in Lin⁻ cells from mice treated with the TGFβ neutralizing antibody, 1D11, supporting a mechanistic link between TGFβ activation and p57 induction. In contrast, TGFβ blockade did not affect p27 upregulation suggesting that p27 is neither a TGFβ target nor a central mediator of HSC quiescence during BM recovery (Cheng et al., *Blood* 98:3643-3649 (2001); Scandura et al., *Proc Natl Acad Sci USA* 101:15231-15236 (2004)).

To further explore the linkage between p57 expression and activation of TGFβ signaling, the inventors FACS-isolated LKS HSPCs prior to and during recovery from chemotherapy in mice treated with 5FU and either the TGFβ neutralizing antibody (1D11) or the control antibody (13C4). The inventors then stained purified LKS⁺ HSPCs for p57 and pSmad2. As previously reported by others, the inventors found p57 expression almost exclusively in the LKS compartment during steady-state hematopoiesis. Only a subset of homeostatic LKS⁺ HSPCs expressed p57 (consistent with Yamazaki et al., 2006) and staining for pSmad2 was weak in these cells suggesting that p57 expression may be mediated by other signaling pathways during homeostasis (see, e.g., Yoshihara et al., 2007). In contrast, both p57 and pSmad2 significantly increased during recovery from hematopoietic stress in HSPCs isolated from mice treated with the control antibody but not in those treated with the 1D11 TGFβ-neutralizing antibody (FIG. 5E-F). These results show that during recovery from chemotherapy, p57 is a downstream target of TGFβ in HSPCs.

Role of p57 in Homeostatic Hematopoiesis.

To test whether upregulation of p57 is necessary for the cytostatic effects of TGFβ, the inventors studied an engineered mouse strain that did not express p57 (Zhang et al., *Nature* 387:151-158 (1997)). Of all the CDKIs, p57 is the only one required for life. Mice without p57 (p57-KO) die shortly after birth due to poor feeding, resulting from a cleft palate and other developmental abnormalities. The inventors first generated an EGFP-expressing strain of mice that carried a paternally inherited p57-null allele (Schaefer et al., *Cell Immunol* 214:110-122 (2001)). To study p57-KO hematopoiesis, the inventors then transplanted fetal liver mononuclear cells (FLMCs), obtained from p57-WT and p57-KO littermates (EGFP⁺), into lethally irradiated C57BL/6J recipient mice and allowed them to reach homeostasis. The inventors did not identify significant differences in the number of FLMCs from p57-WT or p57-KO littermates (FIG. 6A) and the chimeric mice engrafted with p57-WT or p57-KO littermate FLMCs had similar BM cellularity (FIG. 6C) and frequency of LKS HSPCs at steady-state (FIG. 6B). HSPCs deficient in p57 (p57-KO) engrafted normally and yielded durable hematopoiesis characterized by a mild, normocytic anemia, and a progenitor pool that was slightly biased towards granulopoiesis (FIG. 6D-E).

p57 Deletion Phenocopies TGFβ Blockade During Hematopoietic Regeneration after Chemotherapy.

Figure 7:
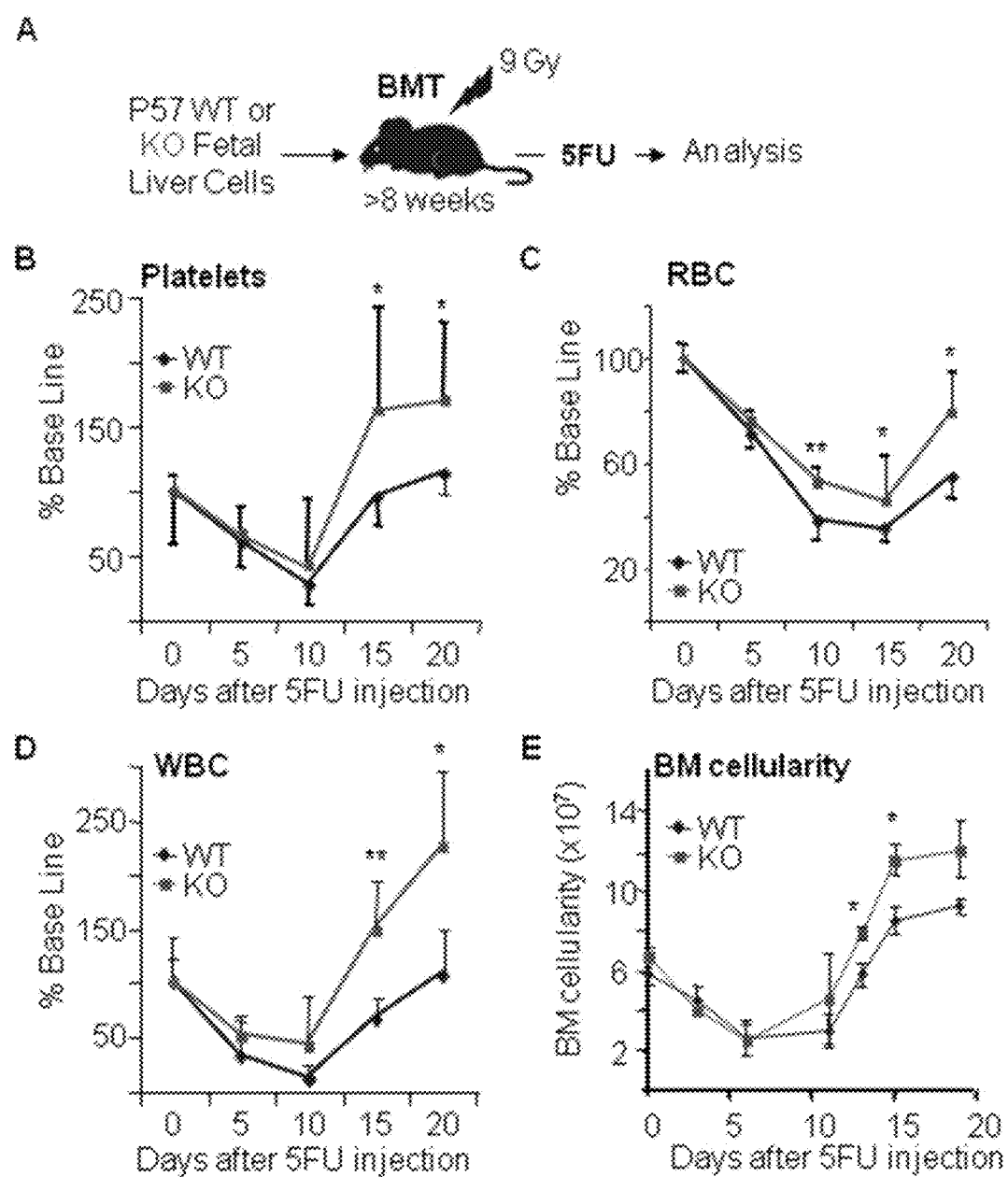
FIG. 7. p57-KO HSPCs recover more robustly after myelosuppressive chemotherapy. (A) Littermate FLMCs were isolated from p57-WT or p57-KO embryos and transplanted into lethally-irradiated C57BL/6J recipient mice (n=10). Once homeostasis was reached (~10 weeks), recipient mice were treated with a single myelosuppressive dose of 5FU (150 mg/kg, i.p) as indicated. Peripheral blood platelets (B), RBCs (C) and WBCs (D) recovered significantly more quickly in mice with p57-KO hematopoiesis, as did BM cellularity (E). All quantified data are shown as mean±SEM (*p<0.05, p<0.01, *p<0.001, or if undesignated, the comparison was not significant).

To assess the role of p57 in the TGFβ-mediated restoration of HSPC quiescence after chemotherapy, the inventors administered 5FU to chimeric mice engrafted with p57-WT or p57-KO HSPCs and then followed hematopoietic regeneration (FIG. 7). Mice with p57-KO hematopoiesis recovered BM and spleen cellularity and peripheral blood counts more rapidly compared to control mice engrafted with p57-WT hematopoiesis (FIG. 7). Thus, similar to TGFβ signaling, p57 restrains hematopoietic recovery after BM stress. Importantly, these results show that the phenotype of p57-KO hematopoiesis is context dependent being mild in homeostasis and substantial during hematopoietic regeneration.

The inventors next used multidimensional flow cytometry to determine whether shifts in HSPC populations explained why deletion of p57 helped to restore hematopoiesis after chemotherapy. At steady-state, the inventors found no significant difference in the HSPC populations but on D15 after chemotherapy, at a time that TGFβ signaling and p57 expression are normally upregulated, the inventors found significantly more LKS$^+$ HSPCs in mice with p57-KO hematopoiesis (FIG. 8A-D). Similar effects were seen in the spleen. The inventors functionally validated the expansion of immature HSPCs/MPPs by analyzing spleen colony-forming units (CFU-S) before and after chemotherapy (FIG. 8E) (McCulloch, CFU-S. In Hematopoietic Stem Cell Protocols. 153-160 (2002)). These results suggest that without p57, immature HSPCs undergo additional rounds of cell division during BM regeneration.

The inventors assessed the cell cycle status of p57-KO and p57-WT HSPCs in homeostatic BM and during recovery from myelosuppressive chemotherapy. The inventors found a small, but statistically significant reduction in the number of quiescent LKS HSPCs in p57-KO chimeric mice (FIG. 8G). Steady-state quiescence is thought to protect HSCs from cell cycle active agents such as 5FU, and more actively cycling HSCs, such as those deficient in p21 (Cdkn1a), are sensitized to the cytotoxic effects of 5FU (Cheng et al., *Science* 287:1804-1808 (2000)). However, chimeric mice with p57-KO hematopoiesis appeared no more sensitive to 5FU than those with p57-WT hematopoiesis as assessed by the collinearity of blood counts (FIG. 7B-D), BM cellularity (FIG. 7E) and LKS HSPC frequency immediately after chemotherapy (D0 to D3). During recovery from myelosuppressive chemotherapy, p57 deletion delays the return to quiescence of LKS$^+$ HSPCs and LKS$^+$ SLAM cells (FIG. 8F-G) but LKS$^-$ hematopoietic progenitors return to quiescence on time. This delay allows greater expansion of HSPCs and faster hematopoietic recovery. Thus, the hematopoietic phenotype of p57 deletion is remarkably similar to the effect of TGFβ blockade during recovery from hematopoietic stress.

Although the cytostatic effects of TGFβ appear to require p57 induction in WT hematopoietic cells, other CDKIs may partially compensate for p57 deletion in the engineered mouse strain (Zou et al., *Cell Stem Cell* 9:247-261 (2011)). The inventors quantified the relative mRNA expression of CDKIs known to affect HSC function in immature hematopoietic cells purified from mice engrafted with p57-WT or p57-KO HSCs. The inventors did not identify basal differences in the expression of p21, p27 or p18 in the p57-KO mice, suggesting that other CDKIs do not compensate for deletion of p57 in the knockout strain studied (Zhang et al., *Nature* 387:151-158 (1997)) (FIG. 8H). More importantly, the inventors found that no stress-induced changes in the expression of CDKIs other than p57 could explain the phenotype of mice with p57-KO hematopoiesis, suggesting that these effects are specific to p57. These results indicate that p57 safeguards HSC quiescence during homeostasis and helps restore quiescence during hematopoietic regeneration.

TGFβ Blockade During Recovery from Hematopoietic Stress Delays HSC Quiescence.

Figure 11:
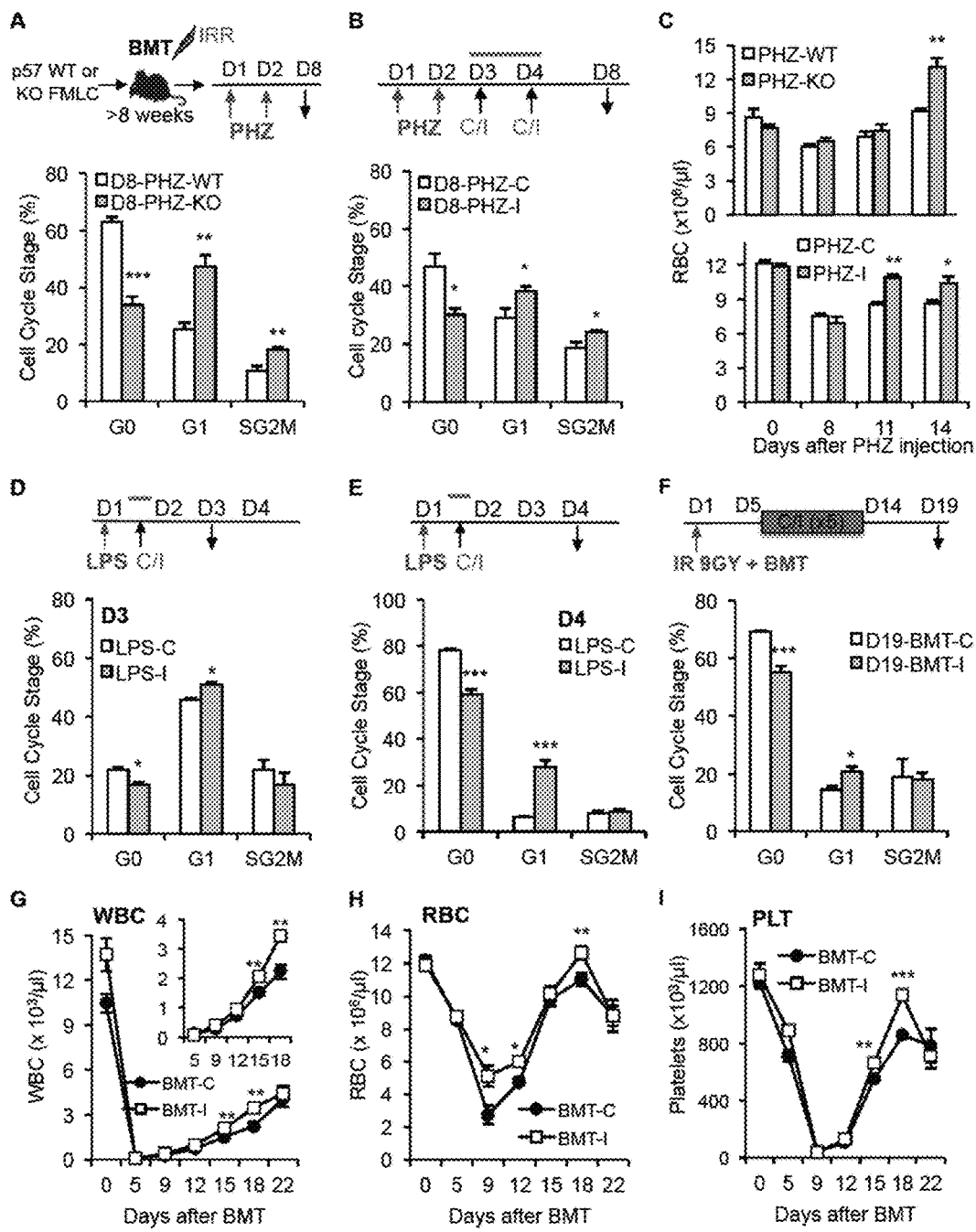
FIG. 11. Blockade of TGFβ during recovery from hematologic stress prolongs HSPC cycling. (A) Chimeric mice with p57-WT or p57-KO hematopoiesis were injected with phenylhydrazine hydrochloride (PHZ) on D1 and D2 and then killed on D8 for LKS+SLAM cell cycle analysis. (B) C57BL/6J mice were injected with PHZ as previously described and then with either the TGFβ-neutralizing antibody 1D11 (I) or control antibody 13C4 (C) on D3 and D4. Mice were then killed on D8 and analyzed as described previously. (C) C57BL/6J mice were injected with lipopolysaccharides (LPS) on D1 and then with either 1D11 (I) or 13C4 (C) 6 hours later. Cell cycle status of LKS+SLAM cells was analyzed on D3 (C) and D4 (D) after LPS administration. (E) Lethally irradiated mice were transplanted with 2×106 WT BMMCs on D1 and then administered either 1D11 (I) or 13C4 (C) on D7, D9, D11 and D14 after transplantation. Mice were sacrificed on D19 for LKS+SLAM cell cycle analysis. All quantified data are shown as mean±SEM (*p<0.05, p<0.01, *p<0.001, or if undesignated, the comparison was not significant).

Because the TGFβ/p57 axis induces HSCs to return to quiescence after myelosuppressive chemotherapy, the inventors investigated if this pathway served a similar role in restoring homeostasis following other hematopoietic stresses. The inventors used phenylhydrazine (PHZ) to trigger massive hemolysis and to recruit HSCs into cell cycle. To determine if p57 functions in the restoration of HSC quiescence after hemolysis, the inventors treated chimeric mice, stably engrafted with p57-KO or p57-WT hematopoiesis, with PHZ and then and killed the mice on D8 to analyze the cell cycle of BM LKS+SLAM cells (FIG. 11A). During recovery from acute hemolysis, LKS+SLAM cells from mice with p57-KO hematopoiesis delayed their return to quiescence when compared to WT controls. Similarly, it was found that TGFβ blockade with 1D11 (I) after acute hemolysis delayed the return of LKS+SLAM cells to quiescence when compared to mice treated with the 13C4 control antibody (C) (FIG. 11B). Whether TGFβ signaling was blocked by neutralizing the ligand (1D11) or by genetically deleting its downstream mediator (p57-KO), red blood cell counts recovered more quickly after hemolysis (FIG. 11C). The inventors next used lipopolysaccharide (LPS) to model an overwhelming infection and determine if TGFβ signaling in this setting also restored HSC quiescence (FIG. 11D). LKS+SLAM cells from mice that received a single dose of 1D11 after LPS had significantly prolonged cycling implicating TGFβ signaling as a trigger inducing quiescence during recovery from infection (FIG. 11D-E). The inventors also studied how TGFβ blockade altered the kinetics of HSC cycling after syngeneic bone marrow transplantation (BMT) using lethal irradiation as conditioning. The inventors transplanted recipient mice with 2 million BM cells from WT donors and then administered 1D11 (I) or 13C4 (C) every 2-3 days between D5 and D14 prior to sacrificing the recipients on D19 for cell cycle analysis (FIG. 11F). As seen for other stressors, a greater proportion of LKS+SLAM cells were actively cycling when TGFβ signaling was blocked during recovery from the hematopoietic stress of engraftment. Significantly, blood counts recovered more quickly when TGFβ signaling was inhibited during 12 engraftment (FIG. 11G-I). Thus, the inventors concluded that the TGFβ/p57 axis is commonly employed to re-establish HSC quiescence during recovery from hematopoietic stress.

Hematopoietic Stress Provides p57-KO HSCs with a Context-Dependent Competitive Advantage.

Figure 9:
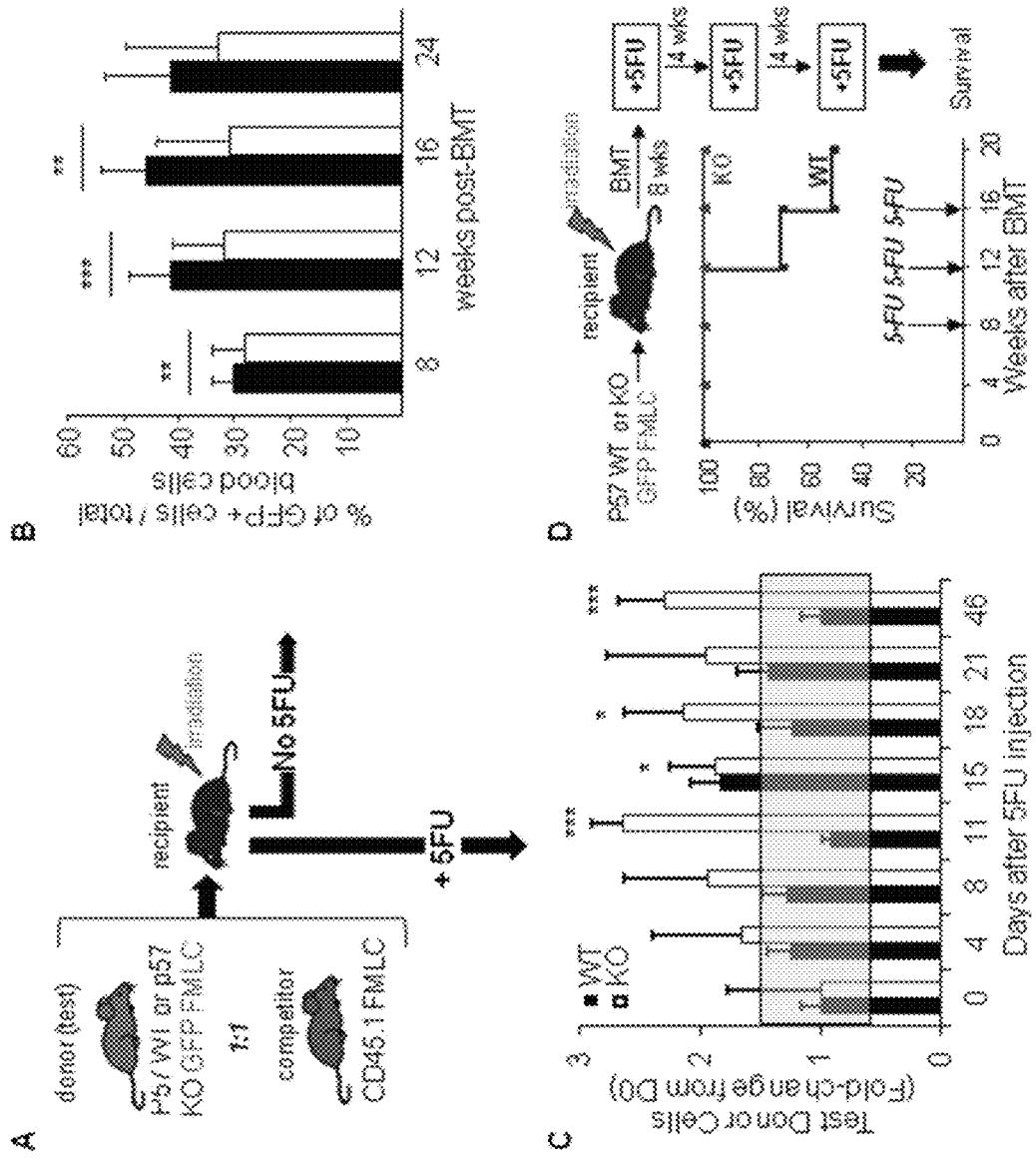
FIG. 9. Hematopoietic stress confers a competitive advantage to p57-KO HSCs. (A) Schematic representation of competitive repopulation unit (CRU) analysis. CD45.1+ control FLMCs were mixed 1:1 with a test population of either p57-WT and p57-KO FLMCs (EGFP+/+) and then transplant into lethally-irradiated recipient mice (n=10). Stably engrafted mice with p57-WT or p57-KO hematopoiesis were analyzed at steady-state (B) or after chemotherapy (C). (B) Multilineage peripheral blood engraftment was analyzed by flow cytometry at the indicated times after reconstitution to assess the proportion of p57-WT or p57-KO cells (n=10). (C) To study the effect of myelosuppressive stress in competitively transplanted recipient mice, recipients were allowed to reach homeostasis (10 weeks) and then given a single dose of myelosuppressive chemotherapy. Multilineage engraftment was assessed as described previously to monitor the relative contribution of p57-WT or p57-KO hematopoiesis during regeneration (n=10). The percentage of donor cells was normalized to the D0 measure for each mouse. Stress conferred an advantage to p57-KO hematopoietic cells during recovery with the changes meeting statistical significance after D11. The orange box represents the standard deviation of the D0 measurements. (D) Kaplan-Meier survival curve shows that p57-KO hematopoiesis is more tolerant of cyclic chemotherapy. Stably engrafted mice with p57-WT or p57-KO hematopoiesis (n=10) were treated every 4 weeks with a myelosuppressive dose of 5FU. All quantified data are shown as mean±SEM (*p<0.05, p<0.01, *p<0.001, or if undesignated, the comparison was not significant).

The inventors examined the possibility that p57-KO HSPCs are inherently proliferative by competitively transplanting C57B1/6J recipient mice with a 1:1 mixture of congenic CD45.1 FLMCs and either p57-WT or p57-KO littermate CD45.2/EGFP$^+$ FLMCs (FIG. 9A). The inventors then monitored multilineage engraftment in the blood of the recipient animals for 6 months. Unlike p18-KO HSCs that progressively overrun WT HSCs (Yuan et al., *Nat Cell Biol* 6:436-442 (2004)), p57-KO cells did not unreservedly self-renew during homeostasis; in fact, they were foud slightly underrepresented compared to their littermate p57-WT controls (FIG. 9B).

Interfering with TGFβ signaling after chemotherapy delays the return to quiescence and permits additional rounds of HSPC cell division during hematopoietic regeneration. Chimeric mice with p57-KO hematopoiesis partially phenocopy this delay because genetic deletion of p57 in HSCs extinguishes this module of TGFβ-mediated signaling in the context of hematopoietic recovery. To test the durability of this stress-induced cycling, the inventors administered chemotherapy to mice 10 weeks after competitively engrafting them with p57-KO or p57-WT HSCs, as described previously. The inventors then monitored the relative contribution of each genotype—marked by CD45 isotypes and EGFP—during recovery from myelotoxic stress (FIG. 9C). The proportion of p57-WT test cells remained fixed during recovery from chemotherapy (black bars). This is the expected result because p57-WT (CD45.2/EGFP$^+$) test cells differ from the congenic p57-WT (CD45.1/EGFP$^-$) control cells only in their expression of marker genes. In striking contrast, the proportion of p57-KO test cells rose ~2-fold by D11 after chemotherapy and this effect persisted for almost 7 weeks (the longest time point we analyzed). This result demonstrates that HSPCs unable to induce p57 during hematopoietic regeneration have a cell intrinsic competitive advantage that persists until homeostasis is reestablished. Once homeostasis returns, the p57-KO HSPCs maintain a fixed, albeit expanded, contribution to hematopoiesis.

The data suggest that blockade of TGFβ-induced cytostasis during recovery can be used to limit chemotherapy-induced myelosuppression. To investigate whether blocking TGFβ would delay the upregulation of p57 and permit HSPC cycling to continue thereby sensitizing hematopoiesis to repeated chemotherapy treatments, the inventors treated chimeric mice stably engrafted with p57-WT or p57-KO HSCs with monthly doses of severely myelosuppressive chemotherapy. Whereas three cycles of chemotherapy killed half of the control mice, all mice with p57-KO hematopoiesis survived (FIG. 9D).

Summary of Results

It is shown herein that spatiotemporally-constrained activation of TGFβ signaling in HSPCs helps restore homeostasis after myelosuppressive chemotherapy, and blocking TGFβ after chemotherapy delays homeostasis and accelerates multilineage hematopoietic reconstitution. These results provide the first evidence that hematopoietic homeostasis is actively reimposed during recovery from myelotoxic stress and that blocking TGFβ activation to delay homeostasis can be an effective strategy to limit chemotherapy-induced myelosuppression.

Figure 10:
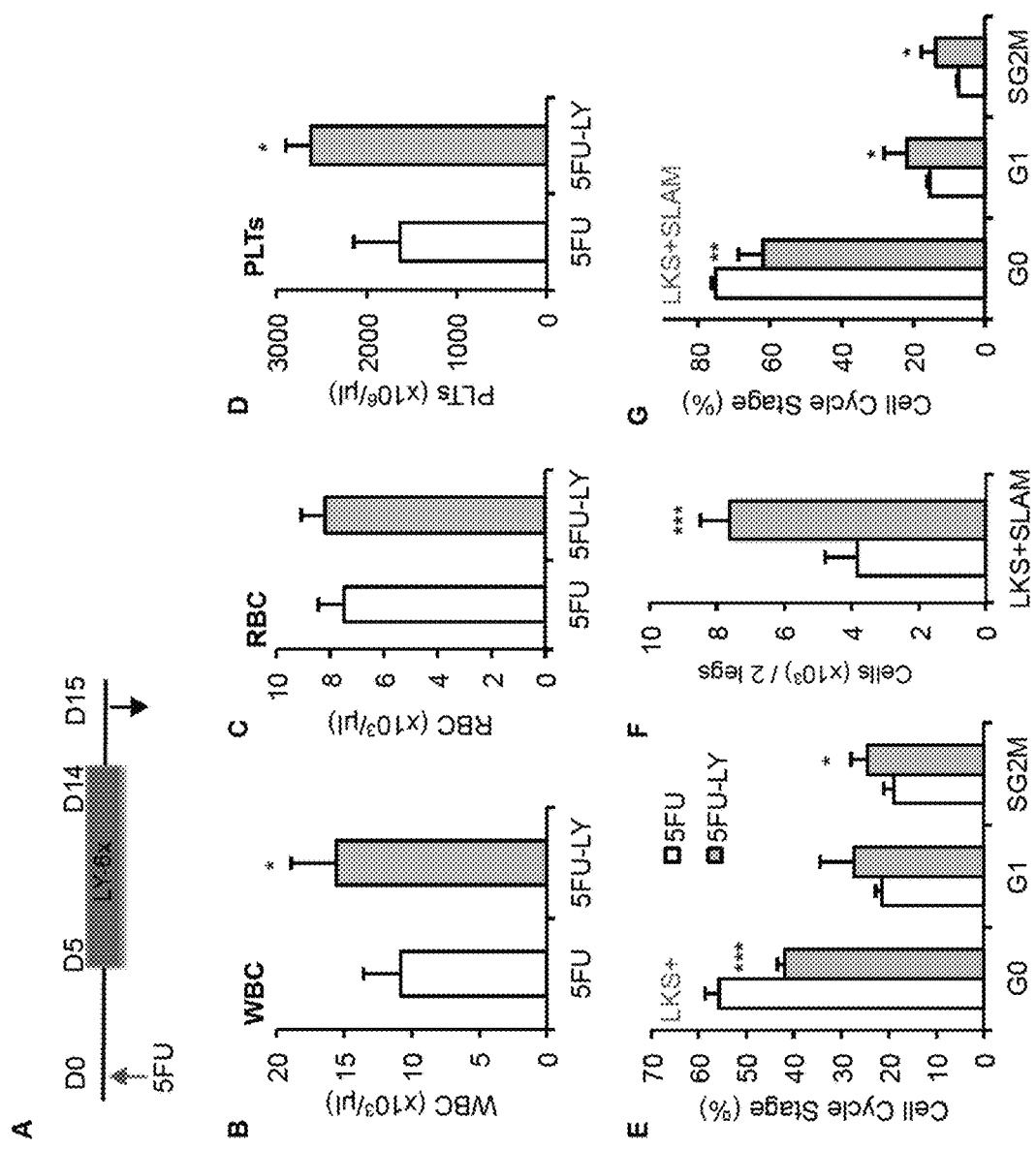
FIG. 10. Inhibition of the TGFβ pathway using an orally-available small molecule enhances hematopoietic recovery after chemotherapy. (A) Mice were treated with 5FU (250 mg/kg) and then either the TGFβ inhibitor (LY364947) or PBS control. 5FU was administrated on D0 followed by once daily IP injections of a selective TGFβ receptor inhibitor (TRI, LY364947) (1 mg/kg) 6 times over a period of 9 days. (B-D) The effect of TGFβ pathway inhibition on blood counts recovery after myelosuppressive chemotherapy of C57BL6 mice is shown (n=5). PLT, WBC recovery was faster when LY364947 was administrated after 5FU. (E, G) Bivariate cell cycle analysis of LKS+ and LKS+SLAM on D15 after treatment with 5FU-LY (grey bars) or 5FU only (white bars) is shown. These cells persisted in cycle after LY364947 treatment whereas normally they have largely returned to a quiescent, G0 state. (F) TGFβ blockade with LY364947 after chemotherapy permitted greater expansion of LKS+SLAM cells compared to control. All data are expressed as mean±SD. P*<0.05, P<0.01, *p<0.001 for +/−LY.

HSCs are predominantly quiescent but they can be rapidly recruited into cell cycle by hematologic stresses such as chemotherapy, infection or bleeding. These triggers set off a remarkable adaptation that sacrifices HSPC quiescence, and the protection it affords, to meet an urgent need for new blood cell production. Growth factors clearly drive HSPC mobilization and proliferation during stress, yet, once the hematopoietic demands have been adequately met, hematopoiesis must return to homeostasis. It has been found herein that the TGFβ pathway helps restore quiescence and that its downstream target, p57, is a central mediator of this effect. Without limiting to any particular theory, the inventors have proposed a model of context-dependent TGFβ activity during hematopoietic regeneration (FIG. 10). At steady-state (Homeostasis), most HSCs are maintained in a quiescent state by niche factors such as TPO, Ang1/2 and possibly TGFβ. During early stress, HSCs are mobilized from the niche and actively cycle throughout early regeneration during which, cytopenias persist and HSPCs proliferate to repopulate the BM. TGFβ signaling is then activated during late regeneration and this re-imposes HSPC quiescence. Transient blockade of TGFβ during late regeneration permits HSPCs to undergo additional rounds of division, while the inhibitor concentration wanes. In the absence of p57, the cytostatic activity of TGFβ is delayed but eventually other, seemingly less potent, TGFβ targets reestablish quiescence.

Although many cell types produce TGFβ, it is secreted as a latent protein in non-covalent complex with the latency-associated peptide (LAP) that prevents it from binding to TGFβ receptors. In turn, LAP interacts with members of the latent TGFβ-binding protein family (LTBP) that can moor the large latent complex in the extracellular matrix. LTBPs influence the release of TGFβ from LAP—a process called activation—to allow TGFβ mediated signaling via cell surface TGFβ receptors (Annes et al., 2003). Latent TGFβ is activated by several mechanisms. LAP can be shed after cleavage by matrix metalloproteinases (MMPs), or plasmin, or through conformational changes induced by reactive oxygen species or adhesive interactions with thrombospondin-1 (TSP1) and integrins (e.g., αvβ6 and αvβ8). Large quantities of latent TGFβ are incorporated into bone matrix (Pfeilschifter et al., *Journal of bone and mineral research: the official journal of the American Society for Bone and Mineral Research* 13:716-730 (1998)). Nonetheless, few BM cells show significant TGFβ signaling during steady-state hematopoiesis (Yamazaki et al., *Cell* 147:1146-1158 (2011)) suggesting that critical aspects of this signaling is regulated by the availability of active TGFβ to its cellular receptors. It has been found herein that active TGFβ levels increase significantly during late hematopoietic regeneration. It is possible that bone marrow remodeling during recovery from chemotherapy could be responsible for context-dependent activation of matrix-associated latent TGFβ.

It is shown herein that context-dependent TGFβ signaling re-establishes HSPC quiescence. This is believed to be the first demonstration of counter-regulation dampening hematopoietic regeneration. The results show that TGFβ blockade during recovery acts by delaying homeostasis and thereby accelerating hematopoietic regeneration. In addition, p57 deletion did not increase the toxicity of monthly myelosuppressive chemotherapy. It is believed that genetic deletion of p57 delays homeostasis but does not prevent other aspects of TGFβ signaling, or other mechanisms of counterregulation, to eventually reestablish HSPC quiescence. Thus, the effects of p57 deletion during regeneration appear transient. Supporting this notion, it has been found that p57 deletion allows HSPCs to outcompete those with intact p57 only during recovery from chemotherapy and this advantage dissipates once homeostasis is reestablished. Thus, it is unlikely that p57 is the only downstream mediator of TGFβ signaling during hematopoietic regeneration. Indeed, the effect of TGFβ blockade on recovery from chemotherapy appeared stronger than that observed in chimeric mice with p57-KO hematopoiesis.

What is claimed is:

1. A method of promoting hematopoietic recovery in a subject, comprising administering a TGFβ signaling inhibitor to the subject, wherein said subject is a cancer patient undergoing chemotherapy with a chemotherapeutic drug, and wherein the TGFβ signaling inhibitor is administered to the subject at least one day after the administration of the chemotherapeutic drug and before the activation of the TGFβ signaling in the bone marrow and within 10 days after the administration of the chemotherapeutic drug.

2. The method of claim 1, wherein the TGFβ signaling inhibitor is administered to the subject at least 2-3 days day after the administration of the chemotherapeutic drug.

3. The method of claim 1, wherein the chemotherapeutic drug is administered to the cancer patient in a higher dosing scheme as compared to the dosing scheme without the TGFβ-pathway inhibitor.

4. The method of claim 3, wherein said higher dosing scheme is selected from a higher dosage amount per dose, a more frequent dosing schedule, a longer treatment cycle, or a combination thereof.

5. The method of claim 1, wherein said subject is undergoing hematopoietic stem cell transplant.

6. The method of claim 1, wherein said subject is suffering an infection which causes hematopoietic stress and/or deficiencies.

7. The method of claim 1, wherein said TGFβ signaling inhibitor is an antibody which antagonizes the interaction and binding between TGFβ and TGFβ receptor.

8. The method of claim 1, wherein said TGFβ signaling inhibitor is a soluble polypeptide composed of the extracellular domain of a TGFβ receptor.

9. The method of claim 1, wherein said TGFβ signaling inhibitor is an oligonucleotide selected from the group consisting of an antisense, RNAi, dsRNA, siRNA and ribozyme molecule.

10. The method of claim 1, wherein said TGFβ signaling inhibitor inhibits TGFβ Receptor kinase activity.

11. The method of claim 1, wherein said TGFβ signaling inhibitor antagonizes the activation of latent TGFβ to its active form capable of binding to a TGFβ receptor.

12. The method of claim 1, wherein the TGFβ signaling inhibitor is administered to the subject within 7 days after the administration of the chemotherapeutic drug.

* * * * *

UNITED STATES PATENT AND TRADEMARK OFFICE
CERTIFICATE OF CORRECTION

PATENT NO. : 9,782,452 B2
APPLICATION NO. : 14/359756
DATED : October 10, 2017
INVENTOR(S) : Scandura et al.

Page 1 of 1

It is certified that error appears in the above-identified patent and that said Letters Patent is hereby corrected as shown below:

In the Specification

Column 1, Line 14 should read:

STATEMENT REGARDING FEDERALLY
SPONSORED RESEARCH OR DEVELOPMENT
This invention was made with government support under Grant No. CA010482 awarded by National Institutes of Health. The government has certain rights in this invention.

Signed and Sealed this
Twenty-fourth Day of April, 2018

Andrei Iancu
*Director of the United States Patent and Trademark Office*